(12) United States Patent
Beraud et al.

(10) Patent No.: US 6,680,369 B2
(45) Date of Patent: Jan. 20, 2004

(54) MOTOR PROTEINS AND METHODS FOR THEIR USE

(75) Inventors: Christophe Beraud, San Francisco, CA (US); Andrew Craven, San Francisco, CA (US); Ming Yu, Foster City, CA (US); Roman Sakowicz, Foster City, CA (US); Umesh A. Patel, Cambridge (GB); Katherine A. Davies, Cambridge (GB)

(73) Assignee: Cytokinetics, Inc., South San Francisco, CA (US)

( * ) Notice: Subject to any disclaimer, the term of this patent is extended or adjusted under 35 U.S.C. 154(b) by 0 days.

(21) Appl. No.: 09/883,096

(22) Filed: Jun. 15, 2001

(65) Prior Publication Data

US 2002/0110883 A1 Aug. 15, 2002

Related U.S. Application Data

(63) Continuation-in-part of application No. 09/594,655, filed on Jun. 15, 2000.

(51) Int. Cl.⁷ ............................................. C07K 14/00
(52) U.S. Cl. ..................................................... 530/350
(58) Field of Search ....................................... 530/350

(56) References Cited

U.S. PATENT DOCUMENTS

| | | | | |
|---|---|---|---|---|
| 6,436,686 B1 * | 8/2002 | Beraud et al. | ............... | 435/196 |
| 6,455,293 B1 * | 9/2002 | Beraud et al. | ............... | 435/196 |
| 6,492,158 B1 * | 12/2002 | Beraud et al. | ............... | 435/196 |
| 6,534,309 B1 * | 3/2003 | Beraud et al. | ........... | 435/320.1 |
| 6,562,610 B1 * | 5/2003 | Beraud et al. | ............... | 435/195 |

OTHER PUBLICATIONS

Skolnick J, et al. Jan. 2000; 18 (1): 34–39.*
AHN et al., "The Structural and functional diversity of dystrophin," Nature Genetics, 3:283–291 (1993).
Burgess et al., "Possible Dissociation of the Heparin–binding and Mitogenic Activities of Heparin0binding (Acidic Fibroblast) Growth Factor–1 from Its Receptor–binding Activities by Site–directed Mutagenesis of a Single Lysine Residue," J. Cell Biol., 111:2129–2138 (1990).
Bork, P., "Powers and pitfalls in sequence analysis: the 70% hurdle," Genome Research, 10:398–400 (2000).
Bowie et al., "Deciphering the Message in Protein Sequences: Tolerance to Amino Acid Substitutions," Science, 247:1306–1310 (1990).
Cawthon et al., "cDNA Sequence and Genomic Structure of EV12B, a Gene Lying within an Intron of the Neurofibromatosis Type 1 Gene," Genomics, 9:446–460 (1991).
Debernardi et al., "Identification of a Novel Human Kinesin–Related Gene (HK2) by the cDNA Differential Display Technique," Genomics, 42:67–73 (1997).
De Plane et al., "Structure, chromosomal localization, and expression of 12 genes of the MAGE family," Immunogenetics, 40:360–369 (1994).

Efferth et al., "Involvement of the kinesin heavy chain in the Sequence dependent synergism of taxol and cisplatin," Proceedings of the American Association for Cancer Research, 37:378, abstract # 2579 (1996).
Gura, T., "Systems for Identifying New Drugs Are Often Faulty," Science, 278:1041–1042 (1997).
Harris et al., "Polycystic Kidney Disease 1: Identification and Analysis of the Primary Defect," J. of American Society of Nephrology, 6:1125–1133 (1995).
Hirokawa et al., "Kinesin and Dynein Superfamily Proteins and the Mechanism of Organelle Transport," Science, 279:519–526 (1998).
Lazar et al., "Transforming Growth Factor α: Mutation of Aspartic Acid 47 and Leucine 48 Results in Different Biological Acitivities," Mol. and Cellular Biol., 8(3):1247–1252 (1988).
Nagai et al., "Identification of the full–length KIAA0591 gene encoding a novel kinesin–related protein which is mapped to the neuroblastoma suppressor gene locus at 1p36.2," Int. J. Oncology, 16:907–916 (2000).
Pereira et al., "Mitochondrial association of a plus end–directed microtubule motor expressed during mitosis in Drosophila," J. Cell Biol., 136:1081–1090 (2000).
Purnelle et al., Genbank Accession # AL023587. Direct Submission, S. pombe chromosome II cosmid c649 (1988).
Reiger et al., Glossary of Genetics and Cytogenetics: Classical and Molecular, 4th edition, Springer–Verlag, Berlin, pp. 17–18 (1976).
Rieger et al., Genbank Accession #Z72739; Y3135. Direct Submission, S. cerevisiae chromosome VII (1996).
Sakowicz et al., "A Marine Natural Product Inhibitor of Kinesin Motors," Science, 280:292–295 (1998).
SIPPEL et al., "Site–directed Mutagenesis within an Ectoplasmic ATPase Consensus Sequence Abrogates the Cell Aggregating Properties of the Rat Liver Canalicular Bile Acid Transporter/Ecto–ATPase/Cell CAM 105 and Carcinoembryonic Antigen*–," J. Biol. Chem., 27(51):33095–33104 (1996).
Stewart et al., Genbank Accession #U89264. Direct submission, Dm Kinesin–like protein 67a (1997).
Sugano et al., GenBank Accession #A W154058, "Cloned polynucleotide sequence encodes a kinesin that has an amino acid Sequence that is 100% identical to SEQ ID BO: 2," (1999).
Tucker et al., "Probing the Kinesin–Microtubule Interaction*," J. Biol. Chem., 272(14):9481–9488 (1997).
Woehlke et al., "Microtubule Interaction Site of the Kinesin Motor," Cell, 90:207–216 (1997).
Wood et al., Genbank Acession #Z97211. Direct Submission. S. pombe chromosome II cosmid c2F12 (1997).
Genbank Accession #BG420786, NIH–MGC http://mgc.nci.hih.gov/. polynucleotide sequence comprises a sequence that is greater than 60% identical to SEQ ID NO: 1 (1999).

* cited by examiner

Primary Examiner—Anthony C. Caputa
Assistant Examiner—Stephen L. Rawlings
(74) Attorney, Agent, or Firm—Lauren L. Stevens; Townsend and Townsend and Crew LLP

(57) ABSTRACT

The invention provides isolated nucleic acid and amino acid sequences of HsKip3, antibodies to HsKip3, methods of screening for HsKip3a modulators using biologically active HsKip3, and kits for screening for HsKip3a modulators.

11 Claims, 11 Drawing Sheets

```
    GCGGCCGCGAATTCGGCACCAGGGGCGCTCTCTCCCGGTGTGGGTACTGCTGTCTGTGGT
  1 ---------+---------+---------+---------+---------+---------+ 60

GTGGCTGTGGGACCCGTGAGCAAGCAGCGACGCCAGCGGCGGAGAACCGACGAAAGGTGT
 61 ---------+---------+---------+---------+---------+---------+ 120

CACCACAGTGATGGCAGTGGAGGACAGCACGCTGCAAGTAGTGGTACGGGTGCGGCCCCC
121 ---------+---------+---------+---------+---------+---------+ 180
                MetAlaValGluAspSerThrLeuGlnValValValArgValArgProPr

CACCCCTCGGGAGCTGGACAGTCAGCGGCGGCCAGTGGTTCAGGTGGTGGACGAGCGGGT
181 ---------+---------+---------+---------+---------+---------+ 240
    oThrProArgGluLeuAspSerGlnArgArgProValValGlnValValAspGluArgVa

GCTGGTGTTTAACCCTGAGGAGCCCGATGGAGGGTTCCCTGGCCTGAAATGGGGTGGCAC
241 ---------+---------+---------+---------+---------+---------+ 300
    lLeuValPheAsnProGluGluProAspGlyGlyPheProGlyLeuLysTrpGlyGlyTh

CCATGATGGCCCCAAGAAGAAGGGCAAAGACCTGACGTTTGTCTTTGACCGGGTCTTTGG
301 ---------+---------+---------+---------+---------+---------+ 360
    rHisAspGlyProLysLysLysGlyLysAspLeuThrPheValPheAspArgValPheGl

CGAGGCGGCCACCCAACAGGACGTGTTCCAGCACACCACGCACAGCGTCCTGGACAGCTT
361 ---------+---------+---------+---------+---------+---------+ 420
    yGluAlaAlaThrGlnGlnAspValPheGlnHisThrThrHisSerValLeuAspSerPh

CCTCCAGGGCTACAACTGCTCAGTGTTTGCCTACGGGGCCACCGGGGCTGGGAAGACACA
421 ---------+---------+---------+---------+---------+---------+ 480
    eLeuGlnGlyTyrAsnCysSerValPheAlaTyrGlyAlaThrGlyAlaGlyLysThrHi

CACCATGCTGGGAAGGGAGGGGGACCCCGGCATCATGTACCTGACCACCGTGGAACTGTA
481 ---------+---------+---------+---------+---------+---------+ 520
    sThrMetLeuGlyArgGluGlyAspProGlyIleMetTyrLeuThrThrValGluLeuTy

CAGGCGCCTGGAGGCCCGCCAGCAGGAGAAGCACTTCGAGGTGCTCATCAGCTACCAGGA
541 ---------+---------+---------+---------+---------+---------+ 600
    rArgArgLeuGluAlaArgGlnGlnGluLysHisPheGluValLeuIleSerTyrGlnGl
```

FIG. 1A

```
       GGTGTATAATGAACAGATCCATGACCTCCTGGAGCCCAAGGGGCCCCTTGCCATCCGCGA
601    ---------+---------+---------+---------+---------+---------+ 660
       uValTyrAsnGluGlnIleHisAspLeuLeuGluProLysGlyProLeuAlaIleArgGl

GGACCCCGACAAGGGGGTGGTGGTGCAAGGACTTTCTTTCCACCAGCCAGCCTCAGCCGA
661    ---------+---------+---------+---------+---------+---------+ 720
       uAspProAspLysGlyValValValGlnGlyLeuSerPheHisGlnProAlaSerAlaGl

GCAGCTGCTGGAGATACTGACCAGGGGGAACCGTAACCGCACGCAGCACCCCACTGATGC
721    ---------+---------+---------+---------+---------+---------+ 780
       uGlnLeuLeuGluIleLeuThrArgGlyAsnArgAsnArgThrGlnHisProThrAspAl

CAACGCGACTTCCTCCCGCTCCCATGCCATCTTCCAGATCTTTGTGAAGCAGCAGGACCG
781    ---------+---------+---------+---------+---------+---------+ 840
       aAsnAlaThrSerSerArgSerHisAlaIlePheGlnIlePheValLysGlnGlnAspAr

GGTTCCAGGACTGACCCAGGCTGTCCAGGTGGCCAAGATGAGCCTGATTGACCTGGCTGG
841    ---------+---------+---------+---------+---------+---------+ 900
       gValProGlyLeuThrGlnAlaValGlnValAlaLysMetSerLeuIleAspLeuAlaGl

CTCAGAGCGGGCATCCAGCACCCATGCGAAGGGGGAGCGGCTGCGGGAGGGGGCCAACAT
901    ---------+---------+---------+---------+---------+---------+ 960
       ySerGluArgAlaSerSerThrHisAlaLysGlyGluArgLeuArgGluGlyAlaAsnIl

CAACCGCTCTCTGCTGGCGCTCATCAACGTCCTCAATGCCTTGGCCGATGCAAAGGGCCG
961    ---------+---------+---------+---------+---------+---------+ 1020
       eAsnArgSerLeuLeuAlaLeuIleAsnValLeuAsnAlaLeuAlaAspAlaLysGlyAr

CAAGACCCATGTGCCCTACCGGGACAGCAAACTGACCCGCCTGCTCAAAGACTCCCTCGG
1021   ---------+---------+---------+---------+---------+---------+ 1080
       gLysThrHisValProTyrArgAspSerLysLeuThrArgLeuLeuLysAspSerLeuGl

GGGCAACTGCCGCACAGTGATGATCGCTGCCATCAGCCCCTCCAGCCTGACCTACGAGGA
1081   ---------+---------+---------+---------+---------+---------+ 1120
       yGlyAsnCysArgThrValMetIleAlaAlaIleSerProSerSerLeuThrTyrGluAs

CACGTACAACACCCTCAAATATGCCGACCGGGCCAAGGAGATCAGGCTCTCGCTGAAGAG
1141   ---------+---------+---------+---------+---------+---------+ 1200
       pThrTyrAsnThrLeuLysTyrAlaAspArgAlaLysGluIleArgLeuSerLeuLysSe

CAATGTGACCAGCCTGGACTGTCACATCAGCCAGTATGCTACCATCTGCCAACAGCTCCA
1201   ---------+---------+---------+---------+---------+---------+ 1260
       rAsnValThrSerLeuAspCysHisIleSerGlnTyrAlaThrIleCysGlnGlnLeuGl
```

FIG. 1B

```
      GGCTGAGGTAGCCGCTCTGAGGAAGAAGCTCCAAGTGTATGAGGGGGGAGGCCAGCCCCC
1261  ---------+---------+---------+---------+---------+---------+  1320
      nAlaGluValAlaAlaLeuArgLysLysLeuGlnValTyrGluGlyGlyGlyGlnProPr

ACCACAGGACCTCCCAGGATCTCCCAAGTCGGGACCACCACCAGAACACCTTCCCAGCTC
1321  ---------+---------+---------+---------+---------+---------+  1380
      oProGlnAspLeuProGlySerProLysSerGlyProProProGluHisLeuProSerSe

CCCCTTGCCACCCCACCCTCCCAGCCAGCCCTGCACCCCAGAGCTCCCTGCAGGGCCTAG
1381  ---------+---------+---------+---------+---------+---------+  1440
      rProLeuProProHisProProSerGlnProCysThrProGluLeuProAlaGlyProAr

AGCCCTTCAAGAGGAGAGTCTGGGGATGGAGGCCCAGGTGGAGAGGGCCATGGAAGGGAA
1441  ---------+---------+---------+---------+---------+---------+  1500
      gAlaLeuGlnGluGluSerLeuGlyMetGluAlaGlnValGluArgAlaMetGluGlyAs

CTCTTCAGACCAGGAGCAGTCCCCAGAGGATGAGGATGAAGGCCCAGCTGAGGAGGTTCC
1501  ---------+---------+---------+---------+---------+---------+  1560
      nSerSerAspGlnGluGlnSerProGluAspGluAspGluGlyProAlaGluGluValPr

AACCCAGATGCCAGAGCAGAACCCCACACATGCACTGCCAGAGTCCCCTCGCCTGACCCT
1561  ---------+---------+---------+---------+---------+---------+  1620
      oThrGlnMetProGluGlnAsnProThrHisAlaLeuProGluSerProArgLeuThrLe

GCAGCCCAAGCCAGTCGTGGGCCACTTCTCAGCACGGGAACTGGATGGGGACCGTTCTAA
1621  ---------+---------+---------+---------+---------+---------+  1680
      uGlnProLysProValValGlyHisPheSerAlaArgGluLeuAspGlyAspArgSerLy

GCAGTTGGCCCCTAAAGGTGCTGTGCGTTGCCCAGCGGCAGTACTCCCTGCTCCAAGCAGC
1681  ---------+---------+---------+---------+---------+---------+  1740
      sGlnLeuAlaLeuLysValLeuCysValAlaGlnArgGlnTyrSerLeuLeuGlnAlaAl

CAACCTCCTGACGCCCGACATGATCACAGAGTTTGAGACCCTACAGCAGCTGGTGCAAGA
1741  ---------+---------+---------+---------+---------+---------+  1800
      aAsnLeuLeuThrProAspMetIleThrGluPheGluThrLeuGlnGlnLeuValGlnGl

GGAAAAAATTGAGCCTGGGGCAGAGGCCTTGAGGACTTCAGGCCTGGCCAGGGGGCACC
1801  ---------+---------+---------+---------+---------+---------+  1860
      uGluLysIleGluProGlyAlaGluAlaLeuArgThrSerGlyLeuAlaArgGlyAlaPr

TCTGGCTCAGGAGCTGTGTTCAGAGTCAATCCCTGTGCCGTCTCCTCTCTGCCCAGAGCC
1861  ---------+---------+---------+---------+---------+---------+  1920
      oLeuAlaGlnGluLeuCysSerGluSerIleProValProSerProLeuCysProGluPr
```

FIG. 1C

```
      TCCAGGATACACTGGCCCTGTGACCCGGACTATGGCGAGGCGACTGAGTGGCCCCCTGCA
1921  ---------+---------+---------+---------+---------+---------+ 1980
      oProGlyTyrThrGlyProValThrArgThrMetAlaArgArgLeuSerGlyProLeuHi

CACCCTGGGAATCCCGCCTGGACCCAACTGCACCCCAGCCCAGGGGTCCCGATGGCCCAT
1981  ---------+---------+---------+---------+---------+---------+ 2040
      sThrLeuGlyIleProProGlyProAsnCysThrProAlaGlnGlySerArgTrpProMe

GGAGAAGAAGAGGAGGAGACCAAGCGCCTTGGAGGCAGACAGTCCCATGGCCTCAAAGCG
2041  ---------+---------+---------+---------+---------+---------+ 2100
      tGluLysLysArgArgArgProSerAlaLeuGluAlaAspSerProMetAlaSerLysAr

GGGCACCAAGCGCCAGCGCCAGTCCTTCCTGCCCTGCCTAAGGAGAGGGTCTCTGCCTGA
2101  ---------+---------+---------+---------+---------+---------+ 2160
      gGlyThrLysArgGlnArgGlnSerPheLeuProCysLeuArgArgGlySerLeuProAs

CACCCAACCTTCACAGGGGCCCAGCACCCCCAAAGGAGAAAGGGCCTCCTCCCCCTGCCA
2161  ---------+---------+---------+---------+---------+---------+ 2220
      pThrGlnProSerGlnGlyProSerThrProLysGlyGluArgAlaSerSerProCysHi

TTCCCCTCGCGTTTGCCCAGCCACAGTCATCAAAAGCCGGGTGCCCCTGGGCCCTTCCGC
2221  ---------+---------+---------+---------+---------+---------+ 2280
      sSerProArgValCysProAlaThrValIleLysSerArgValProLeuGlyProSerAl

CATGCAGAACTGCTCCACCCCGCTGGCTCTGCCCACTCGAGACCTCAATGCCACCTTTGA
2281  ---------+---------+---------+---------+---------+---------+ 2340
      aMetGlnAsnCysSerThrProLeuAlaLeuProThrArgAspLeuAsnAlaThrPheAs

TCTCTCTGAGGAGCCTCCCTCAAAGCCCAGTTTCCATGAATGCATTGGCTGGGACAAAAT
2341  ---------+---------+---------+---------+---------+---------+ 2400
      pLeuSerGluGluProProSerLysProSerPheHisGluCysIleGlyTrpAspLysIl

ACCCCAGGAGCTGAGCAGGCTGGACCAGCCCTTCATCCCCAGGGCACCTGTGCCCCTGTT
2401  ---------+---------+---------+---------+---------+---------+ 2460
      eProGlnGluLeuSerArgLeuAspGlnProPheIleProArgAlaProValProLeuPh

CACCATGAAGGGCCCCAAGCCAACATCTTCCCTCCCTGGGACCTCTGCCTGCAAGAAGAA
2461  ---------+---------+---------+---------+---------+---------+ 2520
      eThrMetLysGlyProLysProThrSerSerLeuProGlyThrSerAlaCysLysLysLy

GCGCGTTGCGAGTTCCTCAGTCTCCCATGGCCGCAGCCGCATCGCCCGCCTCCCCAGCAG
2521  ---------+---------+---------+---------+---------+---------+ 2580
      sArgValAlaSerSerSerValSerHisGlyArgSerArgIleAlaArgLeuProSerSe
```

FIG. 1D

```
      CACTTTGAAGAGGCCAGCTGGGCCCCTTGTACTCCCAGAGCTGCCCTTGAGTCCCCTGTG
2581  ---------+---------+---------+---------+---------+---------+ 2640
      rThrLeuLysArgProAlaGlyProLeuValLeuProGluLeuProLeuSerProLeuCy

CCCTAGCAACCGGAGGAATGGAAAGGACCTCATCAGGGTGGGGAGAGCGCTCTCAGCAGG
2641  ---------+---------+---------+---------+---------+---------+ 2700
      sProSerAsnArgArgAsnGlyLysAspLeuIleArgValGlyArgAlaLeuSerAlaGl

GAACGGCGTCACCAAGGTGTCCTGACCGCCAGAATGTCCTGACCACCAAGGTGTCCTAAC
2701  ---------+---------+---------+---------+---------+---------+ 2760
      yAsnGlyValThrLysValSer

CTACCGGCCCCTCTGCTGGATACCCCTCTTGGACCTGTAGCCACCTGCACCAGGAGCTGG
2761  ---------+---------+---------+---------+---------+---------+ 2820

ACCTGCCTTCCTTACCTGGGAGCAATTAGTGCCAACACACCTTTGCTGTATTAACATCCC
2821  ---------+---------+---------+---------+---------+---------+ 2880

TCCCCAGACATCCATCCTGCTACTCACCCTCTGTTAATCTCCTGTTACACTCAGCTTCTT
2881  ---------+---------+---------+---------+---------+---------+ 2940

GGCATGTACATATTCATTTGTGAGTGTTAATGTGCTGCTGTTTTTGTTTTTTGGTGGTT
2941  ---------+---------+---------+---------+---------+---------+ 3000

TTTGTTTTTTGTTTTTTTTGTTTTGAGATGGAGTCTTACTCTGTCGCCCAGGCTGGAGTG
3001  ---------+---------+---------+---------+---------+---------+ 3060

CAGTGGTACGATCTTGGCTCACTGCAACCTCCGCCTCCTGGGTTCAAGTAATTCTCCTGC
3061  ---------+---------+---------+---------+---------+---------+ 3120

CTCAGCTTTCCAAGTAGCTGGGATTACAGGCACCCATCACCACACCCAGCTAATTTTCGT
3121  ---------+---------+---------+---------+---------+---------+ 3180

CTTTTTAATAGAGAGGGGGTTTTTCCATGTTGGCCAGGCTGGTCTTGAACTCCTGACCTC
3181  ---------+---------+---------+---------+---------+---------+ 3240

AGGTGATCCGCCTGCCTCAGCTTCCCAAAGTGCTGAGATTACAGGCATGAGCTACCACGC
3241  ---------+---------+---------+---------+---------+---------+ 3300

CTGGCCCGTGTTGCTGTTTTAAAGGTGCTGCCATGTTCCCCCATCTTTTTTTTTTTGAG
3301  ---------+---------+---------+---------+---------+---------+ 3360
```

FIG. 1E

```
        ATGGAGTCTCGCTCTGTCGCCCAGGCTGGAGTGCAGTGGTGGCGATCTTGGCTCACTGCA
3361    ---------+---------+---------+---------+---------+---------+ 3420

AGCTCCGCCTCCCAGGTTCACACCATTCTCCTGCCTCAGCCTCCCAAGTAGCTGGGACTA
3421    ---------+---------+---------+---------+---------+---------+ 3480

CAGGCGCCCACCACCACGCCCGGCTAATTTTTTGTATTTTTAGTAGAGATGGGGTTTCAC
3481    ---------+---------+---------+---------+---------+---------+ 3540

CGTGTTAGCCAGGCTGGTCTCGATCTGACCTCATGATCCACCCGCCTCGGCCTCCCAAAG
3541    ---------+---------+---------+---------+---------+---------+ 3600

TGCTGGGATTACAGGCGTGAGCCACTGCGCCCGGCCTCCCCTCTCATTTATGATGCCCTC
3601    ---------+---------+---------+---------+---------+---------+ 3660

TGTGCAGGCAGACGGCTCTTGGGCTCTTTTCCCCACCTGTCTCTAACACAGGCCCCACGG
3661    ---------+---------+---------+---------+---------+---------+ 3720

TGATGGCCACAGGCAGTAGAGGAGGAATGAGGATGGGTTGGGGAGCGGGGAGTCGCGGCT
3721    ---------+---------+---------+---------+---------+---------+ 3780

TGGCTCTTCCTGGTTTCTGAGAGGGACATCTTCATCCCTACTCCCCTTGGTCCCCAACCA
3781    ---------+---------+---------+---------+---------+---------+ 3840

CAGTCCTGGTGAAGATGTGGATGATAATGGTGCCTTGATTTCCAAATGAAGACAGCTTTA
3841    ---------+---------+---------+---------+---------+---------+ 3900

TTGCTTAACTCTATTGTACATAGGATACACGTTCAGTGTAAAATAAAGTGTAAAGGGGAA
3901    ---------+---------+---------+---------+---------+---------+ 3960

TTCAGGCTTAATGCTGCACCTAGATATAAATGCTAATGATACTTGGGTTTATAGCCTTCT
3961    ---------+---------+---------+---------+---------+---------+ 4020

GATCCTTTATTTCTGCATATATATATAGATATATACATATATTTTTGGTATAACAATAAA
4021    ---------+---------+---------+---------+---------+---------+ 4080

CCGTCTCCATCCTTGGGAAAAAAAAAAA
4081    ---------+---------+------ 4108
```

FIG. 1F

```
  1 GACAGCACGC TGCAAGTAGT GGTACGGGTG CGGCCCCCCA CCCCTCGGGA GCTGGACAGT
 61 CAGCGGCGGC CAGTGGTTCA GGTGGTGGAC GAGCGGGTGC TGGTGTTTAA CCCTGAGGAG
121 CCCGATGGAG GGTTCCCTGG CCTGAAATGG GGTGGCACCC ATGATGGCCC CAAGAAGAAG
181 GGCAAAGACC TGACGTTTGT CTTTGACCGG GTCTTTGGCG AGGCGGCCAC CCAACAGGAC
241 GTGTTCCAGC ACACCACGCA CAGCGTCCTG GACAGCTTCC TCCAGGGCTA CAACTGCTCA
301 GTGTTTGCCT ACGGGGCCAC CGGGGCTGGG AAGACACACA CCATGCTGGG AAGGGAGGGG
361 GACCCCGGCA TCATGTACCT GACCACCGTG AACTGTACA GGCGCCTGGA GGCCCGCCAG
421 CAGGAGAAGC ACTTCGAGGT GCTCATCAGC TACCAGGAGG TGTATAATGA ACAGATCCAT
481 GACCTCCTGG AGCCCAAGGG GCCCCTTGCC ATCCGCGAGG ACCCCGACAA GGGGGTGGTG
541 GTGCAAGGAC TTTCTTTCCA CCAGCCAGCC TCAGCCGAGC AGCTGCTGGA GATACTGACC
601 AGGGGGAACC GTAACCGCAC GCAGCACCCC ACTGATGCCA ACGCGACTTC CTCCCGCTCC
661 CATGCCATCT TCCAGATCTT TGTGAAGCAG CAGGACCGGG TTCCAGGACT GACCCAGGCT
721 GTCCAGGTGG CCAAGATGAG CCTGATTGAC CTGGCTGGCT CAGAGCGGGC ATCCAGCACC
781 CATGCGAAGG GGGAGCGGCT GCGGGAGGGG GCCAACATCA ACCGCTCTCT GCTGGCGCTC
841 ATCAACGTCC TCAATGCCTT GGCCGATGCA AAGGGCCGCA AGACCCATGT GCCCTACCGG
901 GACAGCAAAC TGACCCGCCT GCTCAAAGAC TCCCTCGGGG GCAACTGCCG CACAGTGATG
961 ATCGCTGCCA TCAGCCCCTC CAGCCTGACC TACGAGGACA CGTACAACAC CCTC
```

FIG. 2

```
  1 DSTLQVVVRV RPPTPRELDS QRRPVVQVVD ERVLVFNPEE PDGGFPGLKW GGTHDGPKKK
 61 GKDLTFVFDR VFGEAATQQD VFQHTTHSVL DSFLQGYNCS VFAYGATGAG KTHTMLGREG
121 DPGIMYLTTV ELYRRLEARQ QEKHFEVLIS YQEVYNEQIH DLLEPKGPLA IREDPDKGVV
181 VQGLSFHQPA SAEQLLEILT RGNRNRTQHP TDANATSSRS HAIFQIFVKQ QDRVPGLTQA
241 VQVAKMSLID LAGSERASST HAKGERLREG ANINRSLLAL INVLNALADA KGRKTHVPYR
301 DSKLTRLLKD SLGGNCRTVM IAAISPSSLT YEDTYNTL
```

FIG. 3

MAVEDSTLQVVVRVRPPTPRELDSQRRPVVQVVDERVLVFNPEEPDGGFPGLKWGGT
HDGPKKKGKDLTFVFDRVFGEAATQQDVFQHTTHSVLDSFLQGYNCSVFAYGATGAG
KTHTMLGREGDPGIMYLTTVELYRRLEARQQEKHFEVLISYQEVYNEQIHDLLEPKG
PLAIREDPDKGVVVQGLSFHQPASAEQLLEILTRGNRNRTQHPTDANATSSRSHAIF
QIFVKQQDRVPGLTQAVQVAKMSLIDLAGSERASSTHAKGERLREGANINRSLLALI
NVLNALADAKGRKTHVPYRDSKLTRLLKDSLGGNCRTVMIAAISPSSLTYEDTYNTL
KYADRAKEIRL KGNSKLEGKPIPNPLLGLDSTRTGHHHHHH

FIG. 4

ATGGCAGTGGAGGACAGCACGCTGCAAGTAGTGGTACGGGTGCGGCCCCCACCCCT
CGGGAGCTGGACAGTCAGCGGCGGCCAGTGGTTCAGGTGGTGGACGAGCGGGTGCTG
GTGTTTAACCCTGAGGAGCCCGATGGAGGGTTCCCTGGCCTGAAATGGGGTGGCACC
CATGATGGCCCCAAGAAGAAGGGCAAAGACCTGACGTTTGTCTTTGACCGGGTCTTT
GGCGAGGCGGCCACCCAACAGGACGTGTTCCAGCACACCACGCACAGCGTCCTGGAC
AGCTTCCTCCAGGGCTACAACTGCTCAGTGTTTGCCTACGGGGCCACCGGGGCTGGG
AAGACACACACCATGCTGGGAAGGGAGGGGACCCCGGCATCATGTACCTGACCACC
GTGGAACTGTACAGGCGCCTGGAGGCCCGCCAGCAGGAGAAGCACTTCGAGGTGCTC
ATCAGCTACCAGGAGGTGTATAATGAACAGATCCATGACCTCCTGGAGCCCAAGGGG
CCCCTTGCCATCCGCGAGGACCCCGACAAGGGGGTGGTGGTGCAAGGACTTTCTTTC
CACCAGCCAGCCTCAGCCGAGCAGCTGCTGGAGATACTGACCAGGGGGAACCGTAAC
CGCACGCAGCACCCCACTGATGCCAACGCGACTTCCTCCCGCTCCCATGCCATCTTC
CAGATCTTTGTGAAGCAGCAGGACCGGGTTCCAGGACTGACCCAGGCTGTCCAGGTG
GCCAAGATGAGCCTGATTGACCTGGCTGGCTCAGAGCGGGCATCCAGCACCCATGCG
AAGGGGGAGCGGCTGCGGGAGGGGGCCAACATCAACCGCTCTCTGCTGGCGCTCATC
AACGTCCTCAATGCCTTGGCCGATGCAAAGGGCCGCAAGACCCATGTGCCCTACCGG
GACAGCAAACTGACCCGCCTGCTCAAAGACTCCCTCGGGGGCAACTGCCGCACAGTG
ATGATCGCTGCCATCAGCCCCTCCAGCCTGACCTACGAGGACACGTACAACACCCTC
AAATATGCCGACCGGGCCAAGGAGATCAGGCTCA GGGCAATTCGAAGCTTGAAGGT
AAGCCTATCCCTAACCCTCTCCTCGGTCTCGATTCTACGCGTACCGGTCATCATCAC
CATCACCATTGA

FIG. 5

MOTOR PROTEINS AND METHODS FOR THEIR USE

CROSS-REFERENCE TO RELATED APPLICATION

The present application is a continuation-in-part of U.S. Ser. No. 09/594,655 filed Jun. 15, 2000, which is incorporated by reference in its entirety for all purposes.

FIELD OF THE INVENTION

The invention provides isolated nucleic acid and amino acid sequences of HsKip3, methods of detecting HsKip3a and screening for HsKip3a modulators using biologically active HsKip3, and kits for screening for HsKip3a modulators.

BACKGROUND OF THE INVENTION

The kinesin superfamily is an extended family of related microtubule motor proteins. It can be classified into at least 8 subfamilies based on primary amino acid sequence, domain structure, velocity of movement, and cellular function. This family is exemplified by "true" kinesin, which was first isolated from the axoplasm of squid, where it is believed to play a role in anterograde axonal transport of vesicles and organelles (see, e.g., Goldstein, Annu. Rev. Genet. 27:319–351 (1993)). Kinesin uses ATP to generate force and directional movement associated with microtubules (from the minus to the plus end of the microtubule, hence it is a "plus-end directed" motor).

Within this functional group of kinesins resides a group of kinesins from several organisms that share significant sequence homology. These include Drosophila Klp67A, S. pombe BC2F12.13, S. pombe BC649.01c, S. cerevisiae Kip3, and HsKif1c.

Drosophila Klp67A has been shown to be a plus end-directed motor. This activity implicates KPL67A in the localization of mitochondria in undifferentiated cell types. In situ hybridization studies of the KLP67A mRNA during embryogenesis and larval central nervous system development indicate a proliferation-specific expression pattern. When affinity-purified anti-KLP67A antisera are used to stain blastoderm embryos, mitochondria in the region of the spindle asters are labeled. These data suggest that KLP67A is a mitotic motor with the role of positioning mitochondria near the spindle.

The discovery of a new kinesin motor protein, and more particularly, one having sequence homology to KLP67A, and the polynucleotides encoding it satisfies a need in the art by providing new compositions which are useful in the diagnosis, prevention, and treatment of cancer, neurological disorders, and disorders of vesicular transport.

SUMMARY OF THE INVENTION

The present invention is based on the discovery of a new human kinesin motor protein, HsKip3, the polynucleotide encoding HsKip3, and the use of these compositions for the diagnosis, treatment, or prevention of cancer, neurological disorders, and disorders of vesicular transport.

In one aspect, the invention provides an isolated nucleic acid sequence encoding a kinesin superfamily motor protein, wherein the motor protein has the following properties: (i) the protein's activity includes microtubule stimulated ATPase activity; and (ii) the protein has a sequence that has greater than 70% amino acid sequence identity to SEQ ID NO:2 or SEQ ID NO:4 as measured using a sequence comparison algorithm. In one embodiment, the protein further specifically binds to polyclonal antibodies raised against SEQ ID NO:2 or SEQ ID NO:4.

In one embodiment, the nucleic acid encodes HsKip3a or a fragment thereof. In another embodiment, the nucleic acid encodes SEQ ID NO:2 or SEQ ID NO:4. In another embodiment, the nucleic acid has a nucleotide sequence of SEQ ID NO:1 or SEQ ID NO:3.

In one aspect, the nucleic acid comprises a sequence which encodes an amino acid sequence which has greater than 70% sequence identity with SEQ ID NO:2 or SEQ ID NO:4, preferably greater than 80%, more preferably greater than 85% or 90%, more preferably greater than 95% or, in another embodiment, has 98 to 100% sequence identity with SEQ ID NO:2 or SEQ ID NO:4.

In one embodiment, the nucleic acid comprises a sequence which has greater than 55 or 60% sequence identity with SEQ ID NO:1 or SEQ ID NO:3, preferably greater than 70%, more preferably greater than 80%, more preferably greater than 90 or 95% or, in another embodiment, has 98 to 100% sequence identity with SEQ ID NO:1 or SEQ ID NO:3. In another embodiment provided herein, the nucleic acid hybridizes under stringent conditions to a nucleic acid having a sequence or complementary sequence of SEQ ID NO:1 or SEQ ID NO:3.

In another aspect, the invention provides an expression vector comprising a nucleic acid encoding a kinesin superfamily motor protein, wherein the motor protein has the following properties: (i) the protein's activity includes microtubule stimulated ATPase activity; and (ii) the protein has a sequence that has greater than 70% amino acid sequence identity to SEQ ID NO:2 or SEQ ID NO:4 as measured using a sequence comparison algorithm. The invention further provides a host cell transfected with the vector.

In another aspect, the invention provides an isolated kinesin superfamily motor protein, wherein the protein has one or more of the properties described above. In one embodiment, the protein specifically binds to polyclonal antibodies generated against a motor domain, tail domain or other fragment of HsKip3. In another embodiment, the protein comprises an amino acid sequence of SEQ ID NO:2 or SEQ ID NO:4.

In one aspect, the protein provided herein comprises an amino acid sequence which has greater than 70% sequence identity with SEQ ID NO:2 or SEQ ID NO:4, preferably greater than 80% or 85%, more preferably greater than 90%, more preferably greater than 95% or, in another embodiment, has 98 to 100% sequence identity with SEQ ID NO:2 or SEQ ID NO:4.

The invention features a substantially purified polypeptide comprising the amino acid sequence of SEQ ID NO:2 or SEQ ID NO:4 or a fragment thereof and more particularly, the motor domain of the amino acid sequence of SEQ ID NO:2 or a fragment thereof such as SEQ ID NO:4.

In one embodiment, the present invention provides a method of identifying a candidate agent as a modulator of the activity of a target protein. The method comprises adding a candidate agent to a mixture comprising a target protein that directly or indirectly produces ADP or phosphate, under conditions that normally allow the production of ADP or phosphate. The method further comprises subjecting the mixture to a reaction that uses said ADP or phosphate as a substrate under conditions that normally allow the ADP or phosphate to be utilized and determining the level of activity of the reaction as a measure of the concentration of ADP or phosphate. A change in the level between the presence and absence of the candidate agent indicates a modulator of the target protein.

The phrase "use ADP or phosphate" means that the ADP or phosphate are directly acted upon by detection reagents. In one case, the ADP, for example, can be hydrolyzed or can be phosphorylated. As another example, the phosphate can be added to another compound. As used herein, in each of these cases, ADP or phosphate is acting as a substrate.

Preferably, the target protein either directly or indirectly produces ADP or phosphate and comprises a motor domain. More preferably, the target protein comprises a kinesin superfamily motor protein as described above and most preferably, the target protein comprises HsKip3a or a fragment thereof.

Also provided are modulators of the target protein including agents for the treatment of cellular proliferation, including cancer, hyperplasias, restenosis, cardiac hypertrophy, immune disorders and inflammation. The agents and compositions provided herein can be used in variety of applications which include the formulation of sprays, powders, and other compositions. Also provided herein are methods of treating cellular proliferation disorders such as cancer, hyperplasias, restenosis, cardiac hypertrophy, immune disorders and inflammation, for treating disorders associated with HsKip3a activity, and for inhibiting HsKip3.

BRIEF DESCRIPTION OF THE DRAWINGS

FIGS. 1A–1F show a nucleic acid sequence and amino acid sequence of HsKip3a (SEQ ID NO:1 and 2).

FIG. 2: shows a nucleic acid sequence encoding a motor domain fragment of HsKip3a (SEQ ID NO:3).

FIG. 3 shows the amino acid sequence of the motor domain fragment shown in FIG. 2. (SEQ ID NO:4).

FIG. 4 shows the amino acid sequence of the Kip3a fragment used in the ATPase assay. Grayed sequence is derived from the vector (pCRT7/CT, Invitrogen) and contains a V5 epitope and polyhistidine tag (SEQ ID NO:5).

FIG. 5 shows the nucleic acid sequence encoding the amino acid sequence shown in FIG. 4 (SEQ ID NO:6).

DETAILED DESCRIPTION OF THE INVENTION

I. Definitions

Figure 6:
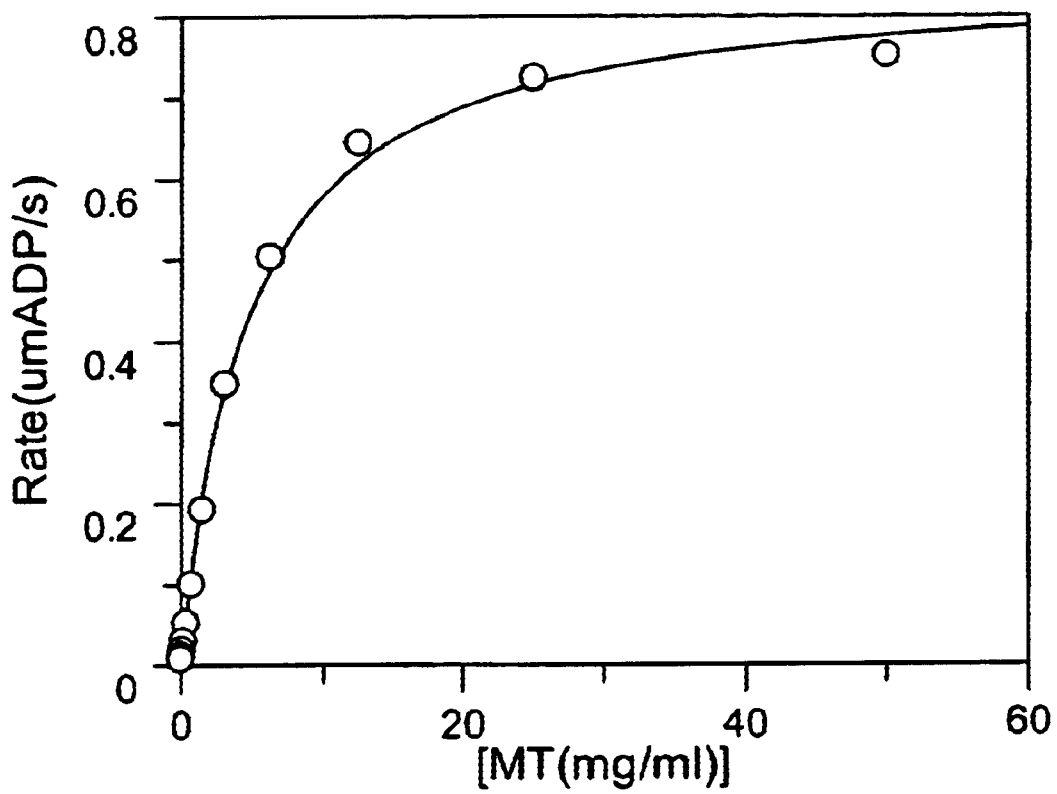
FIG. 6 shows data from an ATPase assay of the motor domain fragment shown in FIG. 4.
Figure 7A:
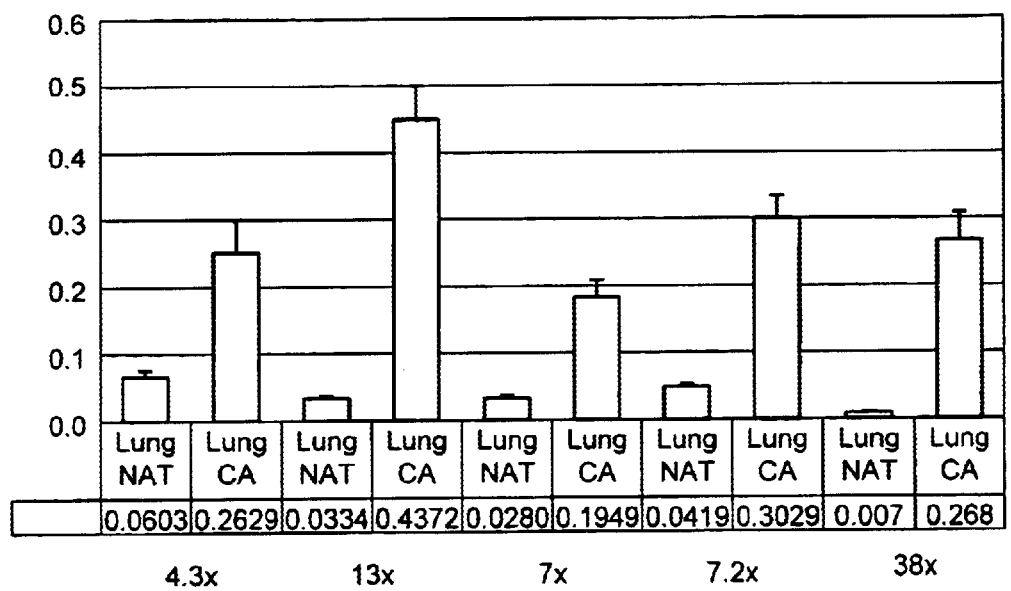
FIG. 7 shows expression profiles of HsKip3a in different tissues.
Figure 7B:
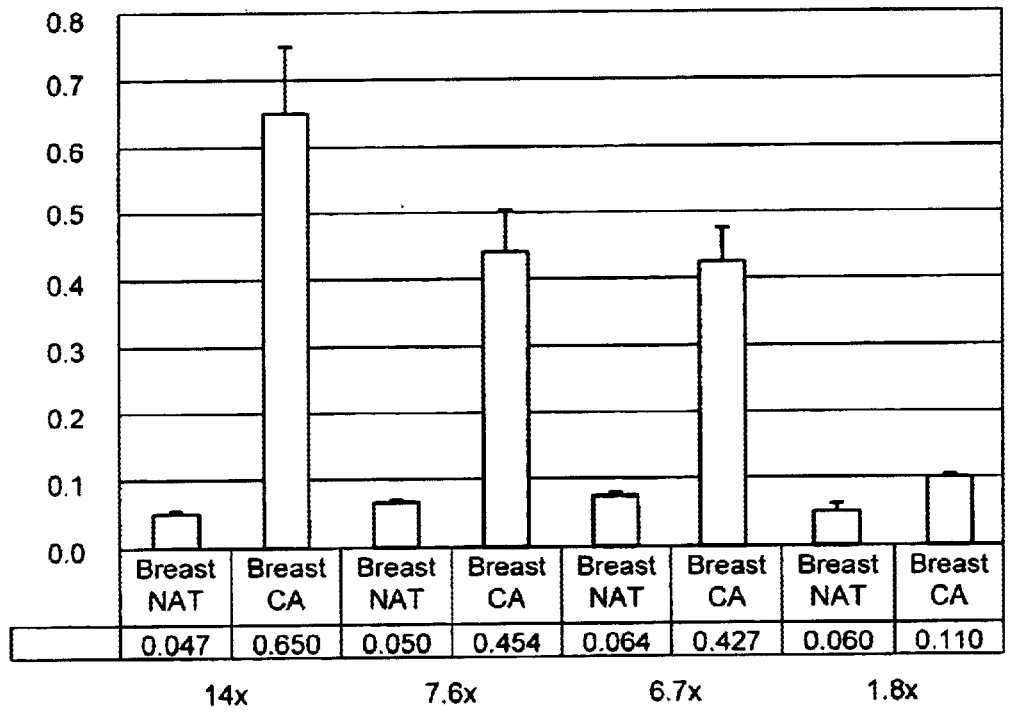
Figure 7C:
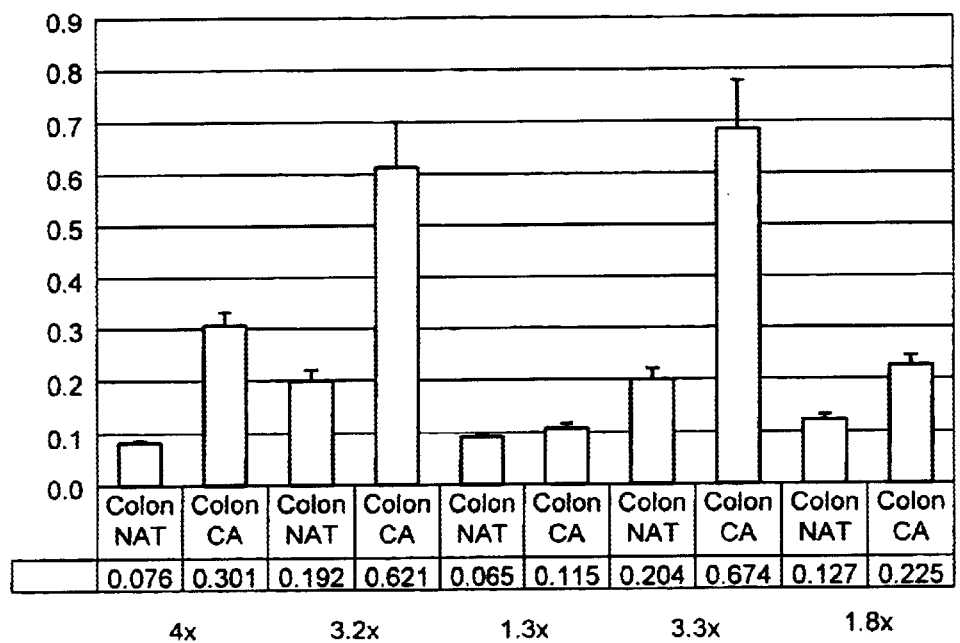
Figure 7D:
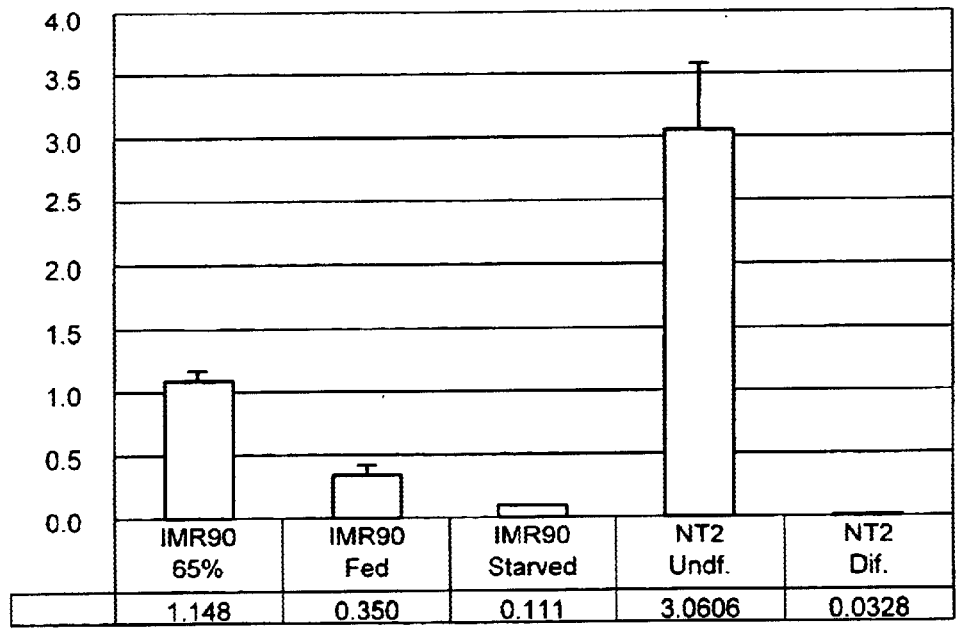

"ADP" refers to adenosine diphosphate and also includes ADP analogs, including, but not limited to, deoxyadenosine diphosphate (dADP) and adenosine analogs.

"Antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. The term antibody also includes antibody fragments either produced by the modification of whole antibodies or those synthesized de novo using recombinant DNA methodologies.

An "anti-HsKip3" antibody is an antibody or antibody fragment that specifically binds a polypeptide encoded by the HsKip3a gene, cDNA, or a subsequence thereof.

"Biologically active" target protein refers to a target protein that has one or more of kinesin protein's biological activities, including, but not limited to microtubule stimulated ATPase activity, as tested, e.g., in an ATPase assay. Biological activity can also be demonstrated in a microtubule gliding assay or a microtubule binding assay. "ATPase activity" refers to ability to hydrolyze ATP. Other activities include polymerization/depolymerization (effects on microtubule dynamics), binding to other proteins of the spindle, binding to proteins involved in cell-cycle control, or serving as a substrate to other enzymes, such as kinases or proteases and specific kinesin cellular activities, such as chromosome congregation, axonal transport, etc.

"Biological sample" as used herein is a sample of biological tissue or fluid that contains a target protein or a fragment thereof or nucleic acid encoding a target protein or a fragment thereof. Biological samples may also include sections of tissues such as frozen sections taken for histological purposes. A biological sample comprises at least one cell, preferably plant or vertebrate. Embodiments include cells obtained from a eukaryotic organism, preferably eukaryotes such as fungi, plants, insects, protozoa, birds, fish, reptiles, and preferably a mammal such as rat, mice, cow, dog, guinea pig, or rabbit, and most preferably a primate such as chimpanzees or humans.

A "comparison window" includes reference to a segment of any one of the number of contiguous positions selected from the group consisting of from 25 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the global alignment algorithm of Needleman & Wunsch, J. Mol. Biol. 48:443 (1970), by the search for similarity methods of Pearson & Lipman, Proc. Natl. Acad. Sci. USA 85:2444 (1988) and Altschul et al. Nucleic Acids Res. 25(17): 3389–3402 (1997), by computerized implementations of these algorithms (GAP, BESTFIT, FASTA, and BLAST in the Wisconsin Genetics Software Package, Genetics Computer Group, 575 Science Dr., Madison, Wis.), or by manual alignment and visual inspection (see, e.g., Ausubel et al., supra).

This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another example of a useful algorithm is PILEUP. PILEUP creates a multiple sequence alignment from a group of related sequences using progressive, pairwise alignments. It can also plot a dendrogram showing the clustering relationships used to create the alignment. PILEUP uses a simplification of the progressive alignment method of Feng & Doolittle, J. Mol. Evol. 35:351–360 (1987). The method used is similar to the method described by Higgins & Sharp, CABIOS 5:151–153 (1989). As a general rule, PileUp can align up to 500 sequences, with any single sequence in the final alignment restricted to a maximum length of 7,000 characters.

The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. A series of such pairwise alignments that includes increasingly dissimilar sequences and clusters of sequences at each iteration produces the final alignment.

"Variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCT all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each degenerate codon in a nucleic acid can be modified to yield a functionally identical molecule. Accordingly, each silent variation of a nucleic acid that encodes a polypeptide is implicit in each described sequence.

Also included within the definition of target proteins of the present invention are amino acid sequence variants of wild-type target proteins. These variants fall into one or more of three classes: substitutional, insertional or deletional variants. These variants ordinarily are prepared by site specific mutagenesis of nucleotides in the DNA encoding the target protein, using cassette or PCR mutagenesis or other techniques well known in the art, to produce DNA encoding the variant, and thereafter expressing the DNA in recombinant cell culture. Variant target protein fragments having up to about 100–150 amino acid residues may be prepared by in vitro synthesis using established techniques. Amino acid sequence variants are characterized by the predetermined nature of the variation, a feature that sets them apart from naturally occurring allelic or interspecies variation of the target protein amino acid sequence. The variants typically exhibit the same qualitative biological activity as the naturally occurring analogue, although variants can also be selected which have modified characteristics.

Amino acid substitutions are typically of single residues; insertions usually will be on the order of from about 1 to about 20 amino acids, although considerably longer insertions may be tolerated. Deletions range from about 1 to about 20 residues, although in some cases, deletions may be much longer.

Substitutions, deletions, and insertions or any combinations thereof may be used to arrive at a final derivative. Generally, these changes are done on a few amino acids to minimize the alteration of the molecule. However, larger characteristics may be tolerated in certain circumstances.

The following six groups each contain amino acids that are conservative substitutions for one another:

1) Alanine (A), Serine (S), Threonine (T);

2) Aspartic acid (D), Glutamic acid (E);

3) Asparagine (N), Glutamine (Q);

4) Arginine (R), Lysine (K);

5) Isoleucine (I), Leucine (L), Methionine (M), Valine (V); and

6) Phenylalanine (F), Tyrosine (Y), Tryptophan (W). (see, e.g., Creighton, *Proteins* (1984)).

"Cytoskeletal component" denotes any molecule that is found in association with the cellular cytoskeleton, that plays a role in maintaining or regulating the structural integrity of the cytoskeleton, or that mediates or regulates motile events mediated by the cytoskeleton. Includes cytoskeletal polymers (e.g., actin filaments, microtubules, intermediate filaments, myosin fragments), molecular motors (e.g., kinesins, myosins, dyneins), cytoskeleton associated regulatory proteins (e.g., tropomysin, alpha-actinin) and cytoskeletal associated binding proteins (e.g., microtubules associated proteins, actin binding proteins).

"Cytoskeletal function" refers to biological roles of the cytoskeleton, including but not limited to the providing of structural organization (e.g., microvilli, mitotic spindle) and the mediation of motile events within the cell (e.g., muscle contraction, mitotic chromosome movements, contractile ring formation and function, pseudopodal movement, active cell surface deformations, vesicle formation and translocation.)

A "diagnostic" as used herein is a compound, method, system, or device that assists in the identification and characterization of a health or disease state. The diagnostic can be used in standard assays as is known in the art.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

"High stringency conditions" may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"High throughput screening" as used herein refers to an assay that provides for multiple candidate agents or samples to be screened simultaneously. As further described below, examples of such assays may include the use of microtiter plates which are especially convenient because a large number of assays can be carried out simultaneously, using small amounts of reagents and samples.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, or plant cells. Both primary cells and cultured cell lines are included in this definition.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. Stringent conditions are sequence-dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH, and nucleic acid concentration) at which 50% of the probes complementary to the target sequence hybridize to the target sequence at equilibrium. Typically, stringent conditions will be those in which the salt concentration is less than about 1.0 M sodium ion, typically about 0.05 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

The terms "identical" or percent "identity", in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. Preferably, the percent identity exists over a region of the sequence that is at least about 25 amino acids in length, more preferably over a region that is 50 or 100 amino acids in length. This definition also refers to the complement of a test sequence, provided that the test sequence has a designated or substantial identity to a reference sequence. Preferably, the percent identity exists over a region of the sequence that is at least about 25 nucleotides in length, more preferably over a region that is 50 or 100 nucleotides in length.

When percentage of sequence identity is used in reference to proteins or peptides, it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. The scoring of conservative substitutions can be calculated according to, e.g., the algorithm of Meyers & Millers, Computer Applic. Biol. Sci. 4:11–17 (1988), e.g., as implemented in the program PC/GENE (Intelligenetics, Mountain View, Calif.).

The terms "isolated", "purified", or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In an isolated gene, the nucleic acid of interest is separated from open reading frames that flank the gene of interest and encode proteins other than the protein of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

A "label" is a composition detectable by spectroscopic, photochemical, biochemical, immunochemical, or chemical means. For example, useful labels include fluorescent proteins such as green, yellow, red or blue fluorescent proteins, radioisotopes such as $^{32}P$, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:2 can be made detectable, e.g., by incorporating a radio-label into the peptide, and used to detect antibodies specifically reactive with the peptide).

A "labeled nucleic acid probe or oligonucleotide" is one that is bound, either covalently, through a linker, or through ionic, van der Waals, or hydrogen bonds to a label such that the presence of the probe may be detected by detecting the presence of the label bound to the probe.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 μg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

"Modulators," "inhibitors," and "activators of a target protein" refer to modulatory molecules identified using in vitro and in vivo assays for target protein activity. Such assays include ATPase activity, microtubule gliding, microtubule depolymerizing activity, and binding activity such as microtubule binding activity or binding of nucleotide analogs. Samples or assays that are treated with a candidate agent at a test and control concentration. The control concentration can be zero. If there is a change in target protein activity between the two concentrations, this change indicates the identification of a modulator. A change in activity, which can be an increase or decrease, is preferably a change of at least 20% to 50%, more preferably by at least 50% to 75%, more preferably at least 75% to 100%, and more preferably 150% to 200%, and most preferably is a change of at least 2 to 10 fold compared to a control. Additionally, a change can be indicated by a change in binding specificity or substrate.

"Molecular motor" refers to a molecule that utilizes chemical energy to generate mechanical force. According to one embodiment, the molecular motor drives the motile properties of the cytoskeleton.

The phrase "motor domain" refers to the domain of a target protein that confers membership in the kinesin superfamily of motor proteins through a sequence identity of approximately 35–45% identity to the motor domain of true kinesin.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. For example, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260)2605–2608 (1985); Cassol et al. 1992; Rossolini et al. Mol. Cell. Probes 8:91–98 (1994)). The term nucleic acid is used interchangeably with gene, cDNA, and mRNA encoded by a gene.

"Nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases. In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. A target protein comprises a polypeptide demonstrated to have at least microtubule stimulated ATPase activity. Amino acids may be referred to herein by either their commonly known three letter symbols or by Nomenclature Commission. Nucleotides, likewise, may be referred to by their commonly accepted single-letter codes, i.e., the one-letter symbols recommended by the IUPAC-IUB.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA box element. A promoter also optionally includes distal enhancer or repressor elements that can be located as much as several thousand base pairs from the start site of transcription. A "constitutive" promoter is a promoter that is active under most environmental and developmental conditions. An "inducible" promoter is a promoter that is under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding moieties typically have an affinity for one another of at least $10^6$ $M^{-1}$. Preferred antibodies for use in diagnostics or therapeutics often have high affinities such as $10^7$, $10^8$, $10^9$ or $10^{10}$ $M^{-1}$. Specific binding to an antibody under such conditions may require an antibody that is selected for its specificity for a particular protein. For example, antibodies raised to HsKip3a with the amino acid sequence encoded in SEQ ID NO:2 can be selected to obtain only those antibodies that are specifically immunoreactive with HsKip3a and not with other proteins, except for polymorphic variants, orthologs, alleles, and closely related homologues of HsKip3. This selection may be achieved by subtracting out antibodies that cross react with molecules, for example, such as C. elegans unc-104 and human Kif1A. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

"Test composition" (used interchangeably herein with "candidate agent" and "test compound" and "test agent") refers to a molecule or composition whose effect on the interaction between one or more cytoskeletal components it is desired to assay. The "test composition" can be any molecule or mixture of molecules, optionally in a carrier.

A "therapeutic" as used herein refers to a compound that is believed to be capable of modulating the cytoskeletal system in vivo which can have application in both human and animal disease. Modulation of the cytoskeletal system would be desirable in a number of conditions including, but not limited to: abnormal stimulation of endothelial cells (e.g., atherosclerosis), solid and hematopoietic tumors and tumor metastasis, benign tumors, for example, hemangiomas, acoustic neuromas, neurofibromas, pyogenic granulomas, vascular malfunctions, abnormal wound healing, inflammatory and immune disorders such as rheumatoid arthritis, Behcet's disease, gout or gouty arthritis, abnormal angiogenesis accompanying: rheumatoid arthritis, psoriasis, diabetic retinopathy, and other ocular angiogenic disease such as, macular degeneration, corneal graft rejection, corneal overgrowth, glaucoma, and Osler Webber syndrome.

II. The Target Protein

The present invention provides for the first time a nucleic acid encoding HsKip3. This protein is a member of the kinesin superfamily of motor proteins. More specifically, the HsKip3a sequence of FIG. 2 shares approximately 50% identity with various members of the Kip3a family, being closest in sequence to D.m. KLP67A (53% identity) and most different in sequence to HsKif1c (40% identity). The predicted structure of HsKip3a comprises an amino-terminal, kinesin-like microtubule "motor" domain.

In one aspect, HsKip3a can be defined by having at least one or preferably more than one of the following functional and structural characteristics. Functionally, HsKip3a will have microtubule-stimulated ATPase activity, and microtubule motor activity that is ATP dependent. HsKip3a activity can also be described in terms of its ability to bind microtubules.

The novel nucleotide sequences provided herein encode HsKip3a or fragments thereof. Thus, in one aspect, the nucleic acids provided herein are defined by the novel proteins provided herein. The protein provided herein comprises an amino acid sequence which has one or more of the following characteristics: greater than 70% sequence identity with SEQ ID NO:2 or SEQ ID NO:4, preferably greater than 80%, more preferably greater than 90%, more preferably greater than 95% or, in another embodiment, has 98 to 100% sequence identity with SEQ ID NO:2 or SEQ ID NO:4. As described above, when describing the nucleotide is terms of SEQ ID NO:1 or SEQ ID NO:3, the sequence identity can be the same percentages or slightly lower due to the degeneracy in the genetic code. The invention also includes fragments of the nucleotide sequence shown in FIGS. 1A–1F having at least 10, 15, 20, 25, 50, 100, 1000 or 2000 contiguous nucleotides from SEQ ID NO:1 or a degenerate form thereof. Some fragments include the motor domain which occurs approximately between positions 5 and 348 of the amino acid sequence in FIGS. 1A–1F (determined by sequence comparison of the motor domain of the other kinesins). Some such fragments can be used as hybridization probes or primers. Unless otherwise apparent from the context, reference to nucleotide sequences shown in the figures or sequence can refer to the sequence shown, its perfect complement or a duplex of the two strands. Also included within the definition of target proteins are amino acid sequence variants of wild-type target proteins.

Portions of the HsKip3a nucleotide sequence may be used to identify polymorphic variants, orthologs, alleles, and homologues of HsKip3. This identification can be made in vitro, e.g., under stringent hybridization conditions and sequencing, or by using the sequence information in a computer system for comparison with other nucleotide sequences. Sequence comparison can be performed using any of the sequence comparison algorithms discussed below, with PILEUP as a preferred algorithm.

As will be appreciated by those in the art, the target proteins can be made in a variety of ways, including both synthesis de novo and by expressing a nucleic acid encoding the protein.

Target proteins of the present invention may also be modified in a way to form chimeric molecules comprising a fusion of a target protein with a tag polypeptide that provides an epitope to which an anti-tag antibody can selectively bind. The epitope tag is generally placed at the amino or carboxyl terminus of the target protein. Provision of the epitope tag enables the target protein to be readily detected, as well as readily purified by affinity purification. Various tag epitopes are well known in the art. Examples include poly-histidine (poly-his) or poly-histidine-glycine (poly-his-gly) tags; the flu HA tag polypeptide and its antibody 12CA5 (see, Field et al. (1988) Mol. Cell. Biol. 8:2159); the c-myc tag and the 8F9, 3C7, 6E10, G4, B7 and 9E10 antibodies thereto (see, Evans et al., (1985) Molecular and Cellular Biology, 5:3610); and the Herpes Simplex virus glycoprotein D (gD) tag and its antibody (see, Paborsky et al., (1990) Protein Engineering, 3:547). Other tag polypeptides include the Flag-peptide (see, Hopp et al. (1988) BioTechnology 6:1204); the KT3 epitope peptide (see, Martine et al. (1992) Science, 255:192); tubulin epitope peptide (see, Skinner (1991) J. Biol. Chem. 266:15173); and the T7 gene 10 protein peptide tag (see, Lutz-Freyermuth et al. (1990) Proc. Natl. Acad. Sci. USA 87:6393.

The biological activity of any of the peptides provided herein can be routinely confirmed by the assays provided herein such as those which assay ATPase activity or microtubule binding activity. In one embodiment, polymorphic variants, alleles, and orthologs, homologues of HsKip3a are confirmed by using a ATPase or microtubule binding assays as known in the art.

The isolation of biologically active HsKip3a for the first time provides a means for assaying for modulators of this kinesin superfamily protein. Biologically active HsKip3a is useful for identifying modulators of HsKip3a or fragments thereof and kinesin superfamily members using in vitro assays such as microtubule gliding assays, ATPase assays (Kodama et al., *J. Biochem.* 99:1465–1472 (1986); Stewart et al., *Proc. Nat'l Acad. Sci. USA* 90:5209–5213 (1993)), and binding assays including microtubule binding assays (Vale et al., Cell 42:39–50 (1985)). In vivo assays and uses are provided herein as well. Also provided herein are methods of identifying candidate agents that bind to HsKip3a and portions thereof.

Some portions or fragments of HsKip3a include at least 7, 10, 15, 20, 35, 50, 100, 250, 300, 350, 500, or 1000 contiguous amino acids from the sequence shown in FIGS. 1A–1F. Some fragments contain fewer than 1000, 500, 250, 100 or 50 contiguous amino acids from the sequence shown in FIGS. 1A–1F. For example, exemplary fragments include fragments having 15–50 amino acids or 100–500 amino acids. Some fragments include a motor domain. The motor domain runs from about amino acid 5 to 342–354. Such fragments typically include the span from amino acid residue 5-342, 5-348, 5-353, or 5-354 of FIGS. 1A–1F or an active portion thereof. Some fragments include amino acids 26–354 of FIGS. 1A–1F. Some fragments include a ligand binding domain of HsKip3a. Nucleic acids encoding such fragments are also included in the invention.

As further described herein, a wide variety of assays, therapeutic and diagnostic methods are provided herein which utilize the novel compounds described herein. The uses and methods provided herein, as further described below have in vivo, in situ, and in vitro applications, and can be used in medicinal, veterinary, agricultural and research based applications.

III. Isolation of the Gene Encoding HsKip3

A. General Recombinant DNA Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from mass spectroscopy, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et al., *Nucleic Acids Res.* 12:6159–6168 (1984). Purification of oligonucleotides is by either native acrylamide gel electrophoresis or by anion-exchange HPLC as described in Pearson & Reanier, *J. Chrom.* 225:137–149 (1983).

The sequence of the cloned genes and synthetic oligonucleotides can be verified after cloning using, e.g., the chain termination method for sequencing double-stranded templates of Wallace et al., *Gene* 16:21–26 (1981).

B. Cloning Methods for the Isolation of Nucleotide Sequences Encoding HsKip3

In general, the nucleic acid sequences encoding HsKip3a and related nucleic acid sequence homologs are cloned from cDNA and genomic DNA libraries or isolated using amplification techniques with oligonucleotide primers. Alternatively, expression libraries can be used to clone HsKip3a and HsKip3a homologues by detected expressed homologues immunologically with antisera or purified antibodies made against HsKip3a that also recognize and selectively bind to the HsKip3a homologue. Finally, amplification techniques using primers can be used to amplify and isolate HsKip3a from DNA or RNA. Amplification techniques using degenerate primers can also be used to amplify and isolate HsKip3a homologues. Amplification techniques using primers can also be used to isolate a nucleic acid encoding HsKip3. These primers can be used, e.g., to amplify a probe of several hundred nucleotides, which is then used to screen a library for full-length HsKip3.

Appropriate primers and probes for identifying the gene encoding homologues of HsKip3a in other species are generated from comparisons of the sequences provided herein. As described above, antibodies can be used to identify HsKip3a homologues. For example, antibodies made to the motor domain of HsKip3a or to the whole protein are useful for identifying HsKip3a homologs.

To make a cDNA library, one should choose a source that is rich in the mRNA of choice, e.g., HsKip3. For example, HsKip3a mRNA is most abundant in peripheral blood lymphocytes and bone marrow, with relatively lower levels of expression in colon, lung, small intestine, skin, placenta, and fetal liver. The mRNA is then made into cDNA using reverse transcriptase, ligated into a recombinant vector, and introduced into a recombinant host for propagation, screening and cloning. Methods for making and screening cDNA libraries are well known (see, e.g., Gubler & Hoffman, Gene 25: 263–269); Sambrook et al., supra; Ausubel et al., supra).

For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180–182 (1977). Colony hybridization is read out as generally described in Grunstein et al., *Proc. Natl. Acad. Sci. USA*, 72:3961–3965 (1975).

An alternative method of isolating HsKip3a nucleic acid and its homologues combines the use of synthetic oligonucleotide primers and amplification of an RNA or DNA template (see U.S. Pat. Nos. 4,683,195 and 4,683,202; PCR Protocols: A guide to Methods and Applications (Innis et al., eds. 1990)). Methods such as polymerase chain reaction and ligase chain reaction can be used to amplify nucleic acid sequences of HsKip3a directly from mRNA, from cDNA, from genomic libraries or cDNA libraries. Degenerate oligonucleotides can be designed to amplify HsKip3a homologues using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of HsKip3a encoding mRNA in physiological samples, for nucleic sequencing or for other purposes. Genes amplified by the PCR reaction can be purified from agarose gels and cloned into an appropriate vector. Gene expression of HsKip3a can also be analyzed by techniques known in the art, e.g., reverse transcription and amplification of mRNA, isolation of total RNA or poly A+RNA, northern blotting, dot blotting, in situ hybridization, RNase protection, quantitative PCR, and the like.

Synthetic oligonucleotides can be used to construct recombinant HsKip3a genes for use as probes or for expression of protein. This method is performed using a series of overlapping oligonucleotides usually 40–120 bp in length, representing both the sense and nonsense strands of the gene. These DNA fragments are then annealed, ligated and cloned. Alternatively, amplification techniques can be used with precise primers to amplify a specific subsequence of the HsKip3a gene. The specific subsequence is then ligated into an expression vector.

The gene for HsKip3a is typically cloned into intermediate vectors before transformation into prokaryotic or eukaryotic cells for replication and/or expression. The intermediate vectors are typically prokaryote vectors or shuttle vectors.

C. Expression in Prokaryotes and Eukaryotes

To obtain high level expression of a cloned gene, such as those cDNAs encoding HsKip3, it is important to construct an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the HsKip3a protein are available in, e.g., *E. coli,* Bacillus sp., and Salmonella (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available. The pET expression system (Novagen) is a preferred prokaryotic expression system.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the HsKip3a encoding nucleic acid in host cells. A typical expression cassette thus contains a promoter operably linked to the nucleic acid sequence encoding HsKip3a and signals required for efficient polyadenylation of the transcript, ribosome binding sites, and translation termination. The nucleic acid sequence encoding HsKip3a may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens.* Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23, and fusion expression systems such as GST and LacZ. Epitope tags can also be added to recombinant proteins to provide convenient methods of isolation, e.g., c-myc or histidine tags.

Expression vectors containing regulatory elements from eukaryotic viruses are typically used in eukaryotic expression vectors, e.g., SV40 vectors, cytomegalovirus vectors, papilloma virus vectors, and vectors derived from Epstein Bar virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 late promoter, CMV promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a HsKip3a encoding sequence under the direction of the polyhedrin promoter or other strong baculovirus promoters.

The elements that are typically included in expression vectors also include a replicon that functions in *E. coli,* a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection or transformation methods are used to produce bacterial, mammalian, yeast or insect cell lines that express large quantities of HsKip3a protein, which are then purified using standard techniques (see, e.g., Colley et al., *J. Biol. Chem.* 264:17619–17622 (1989); *Guide to Protein Purification,* in *Methods in Enzymology,* vol. 182 (Deutscher ed., 1990)).

Transformation of eukaryotic and prokaryotic cells are performed according to standard techniques (see, e.g., Morrison, *J. Bact.,* 132:349–351 (1977); Clark-Curtiss & Curtiss, *Methods in Enzymology,* 101:347–362 (Wu et al., eds, 1983). Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing HsKip3.

After the expression vector is introduced into the cells, the transfected cells are cultured under conditions favoring expression of HsKip3, which is recovered from the culture using standard techniques identified below.

IV. Purification of HsKip3a Protein

Either naturally occurring or recombinant HsKip3a can be purified for use in functional assays. In a preferred embodiment, the target proteins are purified for use in the assays to provide substantially pure samples. Alternatively, the target protein need not be substantially pure as long as the sample comprising the target protein is substantially free of other components that can contribute to the production of ADP or phosphate.

The target proteins may be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography, chromatofocussing, selective precipitation with such substances as ammonium sulfate; and others (see, e.g., Scopes, Protein Purification: Principles and Practice (1982); U.S. Pat. No. 4,673,641; Ausubel et al. supra; and Sambrook et al., supra). For example, the target protein can be purified using a standard anti-target antibody column. Ultrafiltration and diafiltration techniques, in conjunction with protein concentration, are also useful. A preferred method of purification is use of Ni-NTA agarose (Qiagen).

The expressed protein can be purified by standard chromatographic procedures to yield a purified, biochemically active protein. The activity of any of the peptides provided herein can be routinely confirmed by the assays provided herein such as those which assay ATPase activity or microtubule binding activity. Biologically active target protein is useful for identifying modulators of target protein or fragments thereof and kinesin superfamily members using in vitro assays such as microtubule gliding assays, ATPase assays (Kodama et al., J. Biochem. 99:1465–1472 (1986); Stewart et al., Proc. Nat'l Acad. Sci. USA 90:5209–5213 (1993)), and binding assays including microtubule binding assays (Vale et al., Cell 42:39–50 (1985)), as described in detail below.

A. Purification of HsKip3a from Recombinant Bacteria

Recombinant proteins are expressed by transformed bacteria in large amounts, typically after promoter induction; but expression can be constitutive. Promoter induction with IPTG is a preferred method of expression. Bacteria are grown according to standard procedures in the art. Fresh or frozen bacteria cells are used for isolation of protein.

Alternatively, it is possible to purify HsKip3a from bacteria periplasm. After HsKip3a is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

Suitable purification schemes for some specific kinesins are outlined in U.S. Ser. No. 09/295,612, filed Apr. 20, 1999, hereby expressly incorporated herein in its entirety for all purposes.

B. Standard Protein Separation Techniques For Purifying HsKip3 Solubility Fractionation Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of HsKip3a can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

HsKip3a can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. Immunological Detection of HsKip3

In addition to the detection of HsKip3a genes and gene expression using nucleic acid hybridization technology, one can also use immunoassays to detect HsKip3. Immunoassays can be used to qualitatively or quantitatively analyze HsKip3. A general overview of the applicable technology can be found in Harlow & Lane, *Antibodies: A Laboratory Manual* (1988).

A. Antibodies to HsKip3

Methods of producing polyclonal and monoclonal antibodies that react specifically with HsKip3a are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)).

Humanized forms of mouse antibodies can be generated by linking the CDR regions of non-human antibodies to human constant regions by recombinant DNA techniques. See Queen et al., Proc. Natl. Acad. Sci. USA 86, 10029–10033 (1989) and WO 90/07861 (incorporated by reference for all purposes).

Human antibodies can be obtained using phage-display methods. See, e.g., Dower et al., WO 91/17271; McCafferty et al., WO 92/01047. In these methods, libraries of phage are produced in which members display different antibodies on their outersurfaces. Antibodies are usually displayed as Fv or Fab fragments. Phage displaying antibodies with a desired specificity are selected by affinity enrichment to HsKip3a or fragments thereof. Human antibodies against HsKip3a can also be produced from non-human transgenic mammals having transgenes encoding at least a segment of the human immunoglobulin locus and an inactivated endogenous immunoglobulin locus. See, e.g., Lonberg et al., WO93/12227 (1993); Kucherlapati, WO 91/10741 (1991) (each of which is incorporated by reference in its entirety for all purposes). Human antibodies can be selected by competitive binding experiments, or otherwise, to have the same epitope specificity as a particular mouse antibody. Such antibodies are particularly likely to share the useful functional properties of the mouse antibodies. Human polyclonal antibodies can also be provided in the form of serum from human immunized with an immunogenic agent. Optionally, such polyclonal antibodies can be concentrated by affinity purification using HsKip3a as an affinity reagent.

A number of HsKip3a comprising immunogens may be used to produce antibodies specifically reactive with HsKip3. For example, recombinant HsKip3a or a antigenic fragment thereof such as the motor domain, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to HsKip3. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-HsKip3a proteins or even other homologous proteins from other organisms (e.g., *C. elegans* unc-104 or human Kif1A), using a competitive binding immunoassay. Specific polyclonal antisera and monoclonal antibodies will usually bind with a $K_d$ of at least about 0.1 mM, more usually at least about 1 $\mu$M, preferably at least about 0.1 $\mu$M or better, and most preferably, 0.01 $\mu$M or better.

Once HsKip3a specific antibodies are available, HsKip3a can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in Enzyme Immunoassay (Maggio ed., 1980); and Harlow & Lane, supra.

B. Binding Assays

Antibodies can be used for treatment or to identify the presence of HsKip3a having the sequence identity characteristics as described herein. Additionally, antibodies can be used to identify modulators of the interaction between the antibody and HsKip3a as further described below. While the following discussion is directed toward the use of antibodies in the use of binding assays, it is understood that the same general assay formats such as those described for "non-competitive" or "competitive" assays can be used with any compound which binds to HsKip3a such as microtubules or the compounds described in Ser. No. 60/070,772.

In a preferred embodiment, HsKip3 a is detected and/or quantified using any of a number of well recognized immunological binding assays (see, e.g., U.S. Pat. Nos. 4,366,241; 4,376,110; 4,517,288; and 4,837,168). For a review of the general immunoassays, see also Methods in *Cell Biology Volume* 37: *Antibodies in Cell Biology* (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the HsKip3a or antigenic subsequence thereof). The antibody (e.g., anti-HsKip3) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled HsKip3a polypeptide or a labeled anti-HsKip3a antibody. Alternatively, the labeling agent may be a third moiety, such a secondary antibody, that specifically binds to the antibody/HsKip3a complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see generally Kronval et al., *J. Immunol.* 111:1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, preferably from about 5 minutes to about 24 hours.

However, the incubation time will depend upon the assay format, antigen, volume of solution, concentrations, and the like. Usually, the assays will be carried out at ambient temperature, although they can be conducted over a range of temperatures, such as 4° C. to 40° C.

Non-Competitive Assay Formats

Immunoassays for detecting HsKip3a in samples may be either competitive or noncompetitive. Noncompetitive immunoassays are assays in which the amount of antigen is directly measured. In one preferred "sandwich" assay, for example, the anti-HsKip3a antibodies can be bound directly to a solid substrate on which they are immobilized. These immobilized antibodies then capture HsKip3a present in the test sample. HsKip3a is thus immobilized is then bound by a labeling agent, such as a second HsKip3a antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of HsKip3a present in the sample is measured indirectly by measuring the amount of a known, added (exogenous) HsKip3a displaced (competed away) from an anti-HsKip3a antibody by the unknown HsKip3a present in a sample. In one competitive assay, a known amount of HsKip3a is added to a sample and the sample is then contacted with an antibody that specifically binds to HsKip3. The amount of exogenous HsKip3 a bound to the antibody is inversely proportional to the concentration of HsKip3a present in the sample. In a particularly preferred embodiment, the antibody is immobilized on a solid substrate. The amount of HsKip3a bound to the antibody may be determined either by measuring the amount of HsKip3a present in a HsKip3/antibody complex, or alternatively by measuring the amount of remaining uncomplexed protein. The amount of HsKip3a may be detected by providing a labeled HsKip3a molecule.

A hapten inhibition assay is another preferred competitive assay. In this assay the known HsKip3, is immobilized on a solid substrate. A known amount of anti-HsKip3a antibody is added to the sample, and the sample is then contacted with the HsKip3. The amount of anti-HsKip3a antibody bound to the known immobilized HsKip3a is inversely proportional to the amount of HsKip3a present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-reactivity Determinations

Immunoassays in the competitive binding format can also be used for crossreactivity determinations. For example, a protein at least partially encoded by SEQ ID NO:2 can be immobilized to a solid support. Proteins (e.g., C. elegans unc-104 or human Kif1A) are added to the assay that compete for binding of the antisera to the immobilized antigen. The ability of the added proteins to compete for binding of the antisera to the immobilized protein is compared to the ability of HsKip3a encoded by SEQ ID NO:2 to compete with itself. The percent crossreactivity for the above proteins is calculated, using standard calculations. Those antisera with less than 10% crossreactivity with each of the added proteins listed above are selected and pooled.

The cross-reacting antibodies are optionally removed from the pooled antisera by immunoabsorption with the added considered proteins, e.g., distantly related homologues.

The immunoabsorbed and pooled antisera are then used in a competitive binding immunoassay as described above to compare a second protein, thought to be perhaps the protein of this invention, to the immunogen protein (i.e., HsKip3a of SEQ ID NO:2). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NO:2 that is required to inhibit 50% of binding, then the second protein is said to specifically bind to the polyclonal antibodies generated to a HsKip3a immunogen.

Other Assay Formats

Western blot (immunoblot) analysis is used to detect and quantify the presence of HsKip3a in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind HsKip3. The anti-HsKip3a antibodies specifically bind to the HsKip3a on the solid support. These antibodies may be directly labeled or alternatively may be subsequently detected using labeled antibodies (e.g., labeled sheep anti-mouse antibodies) that specifically bind to the anti-HsKip3a antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

Reduction of Non-specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), colorimetric labels such as colloidal gold or colored glass or plastic beads (e.g., polystyrene, polypropylene, latex, etc.) or other labels that can be detected by mass spectroscopy, NMR spectroscopy, or other analytical means known in the art.

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize HsKip3, or secondary antibodies that recognize anti-HsKip3.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple calorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Assays for Modulators of the Target Protein

A. Functional Assays

The activity of biologically active HsKip3a can be assessed using a variety of in vitro or in vivo assays known in the art, e.g., ATPase, microtubule gliding, and microtubule binding, microtubule depolymerization assays (Kodama et al., *J. Biochem.* 99: 1465–1472 (1986); Stewart et al., *Proc. Nat'l Acad. Sci.* USA 90: 5209–5213 (1993); (Lombillo et al., *J. Cell Biol.* 128:107–115 (1995); (Vale et al., *Cell* 42:39–50 (1985)). Methods of performing motility assays are well known (see, e.g., Hall, et al. (1996), Biophys.

J., 71: 3467–3476, Turner et al., 1996, Anal. Biochem. 242 (1):20–5; Gittes et al., 1996, Biophys. J. 70(1): 418–29; Shirakawa et al., 1995, J. Exp. Biol. 198: 1809–15; Winkelmann et al., 1995, Biophys. J. 68: 2444–53; Winkelmann et al., 1995, Biophys. J. 68: 72S, and the like).

A preferred assay for high throughput screening is an ATPase assay with calorimetric detection, e.g., malachite green for end-point detection or coupled PK/LDH for continuous rate monitoring. An exemplary ATPase activity assay utilizes 0.3 M PCA (perchloric acid) and malachite green reagent (8.27 mM sodium molybdate II, 0.33 mM malachite green oxalate, and 0.8 mM Triton X-100). To perform the assay, 10 $\mu$L of reaction is quenched in 90 $\mu$L of cold 0.3 M PCA. Phosphate standards are used so data can be converted to mM inorganic phosphate released. When all reactions and standards have been quenched in PCA, 100 $\mu$L of malachite green reagent is added to the to relevant wells in e.g., a microtiter plate. The mixture is developed for 10–15 minutes and the plate is read at an absorbance of 650 nm. If phosphate standards were used, absorbance readings can be converted to mM Pi and plotted over time. Additionally, ATPase assays known in the art include the luciferase assay.

Another exemplary assay can be performed using the following two specific solutions. Solution A contains 1 mM ATP, 2 mM phosphoenolpyruvate in a working buffer (25 mM Pipes pH 6.8, 2 mM MgCl2, 1 mM EGTA, 1 mM DTT, 5 $\mu$M taxol, 25ppm Antifoam, pH 6.8. Solution B contains 0.6 mM NADH, 0.2 mg/ml BSA, 1:100 dilution of PK/LDH mixture from Sigma, 200 $\mu$g/ml microtubules, 100 nM HsKip3a (i.e. ~2.5 $\mu$g/ml).

To initiate the experiment, 1 $\mu$l of DMSO stock of test compounds is added to each well of the bottom row of a 96-well half area plate. Control wells contain only DMSO alone. 50 $\mu$l of solution A is then added to each well. The solutions are mixed by repeated pipetting, followed by a series of dilution by repeated transferring of 50 $\mu$l of solution between rows. The reaction is initiated by adding 50 $\mu$l of solution B. The plate is then inserted in the reader and absorbance at 340 nM was monitored for 5 min. The observed rate for 50 $\mu$l Solution A+50 $\mu$l Solution B in a half-area plate should be about 100 mOD/min. Optionally, a series of dilution is made and absorbance similarly measured. Similar procedures can be used to study the inhibitory effect of a test agent on the basal (i.e., not microtubule-dependent) ATPase of HsKip3a. In these assays, microtubules are omitted from Solution B, and HsKip3a concentration is increased to at least 2 mM.

Such assays can be used to test for the activity of HsKip3a isolated from endogenous sources or recombinant sources. Furthermore, such assays can be used to test for modulators of HsKip3a. Modulators can increase or decrease activity of HsKip3a. In a preferred embodiment, molecular motor activity is measured by the methods disclosed in Ser. No. 09/314,464, filed May 18, 1999, entitled "Compositions and assay utilizing ADP or phosphate for detecting protein modulators", which is incorporated herein by reference in its entirety. More specifically, this assay detects modulators of any aspect of a kinesin motor function ranging from interaction with microtubules to hydrolysis of ATP. ADP or phosphate is used as the readout for protein activity.

There are a number of enzymatic assays known in the art which use ADP as a substrate. For example, kinase reactions such as pyruvate kinases are known. See, Nature 78:632 (1956) and Mol. Pharmacol. 6:31 (1970). This is a preferred method in that it allows the regeneration of ATP. In one embodiment, the level of activity of the enzymatic reaction is determined directly. In a preferred embodiment, the level of activity of the enzymatic reaction which uses ADP as a substrate is measured indirectly by being coupled to another reaction. For example, in one embodiment, the method further comprises a lactate dehydrogenase reaction under conditions which normally allow the oxidation of NADH, wherein said lactate dehydrogenase reaction is dependent on the pyruvate kinase reaction. Measurement of enzymatic reactions by coupling is known in the art. Furthermore, there are a number of reactions which utilize phosphate. Examples of such reactions include a purine nucleoside phosphorylase reaction. This reaction can be measured directly or indirectly. A particularly preferred embodiments utilizes the pyruvate kinase/lactate dehydrogenase system.

In one embodiment, the detection of the ADP or phosphate proceeds non-enzymatically, for example, by binding or reacting the ADP or phosphate with a detectable compound. For example, phosphomolybdate based assays may be used which involve conversion of free phosphate to a phosphomolybdate complex. One method of quantifying the phosphomolybdate is with malachite green. Alternatively, a fluorescently labeled form of a phosphate binding protein, such as the *E. coli* phosphate binding protein, can be used to measure phosphate by a shift in its fluorescence.

In addition, target protein activity can be examined by determining modulation of target protein in vitro using cultured cells. The cells are treated with a candidate agent and the effect of such agent on the cells is then determined either directly or by examining relevant surrogate markers. For example, characteristics such as mitotic spindle morphology and cell cycle distribution can be used to determine the effect. Thus, in a preferred embodiment, the methods comprise combining a target protein and a candidate agent, and determining the effect of the candidate agent on the target protein. Generally a plurality of assay mixtures are run in parallel with different agent concentrations to obtain a differential response to the various concentrations. Typically, one of these concentrations serves as a negative control, i.e., at zero concentration or below the level of detection.

As will be appreciated by those in the art, the components may be added in buffers and reagents to assay target protein activity and give optimal signals. Since the methods allow kinetic measurements, the incubation periods can be optimized to give adequate detection signals over the background.

In a preferred embodiment, an antifoam or a surfactant is included in the assay mixture. Suitable antifoams include, but are not limited to, antifoam 289 (Sigma). Suitable surfactants include, but are not limited to, Tween, Tritons, including Triton X-100, saponins, and polyoxyethylene ethers. Generally, the antifoams, detergents, or surfactants are added at a range from about 0.01 ppm to about 10 ppm.

A preferred assay design is also provided. In one aspect, the invention provides a multi-time-point (kinetic) assay, with at least two data points being preferred. In the case of multiple measurements, the absolute rate of the protein activity can be determined.

B. Binding Assays

In a preferred embodiment, the binding of the candidate agent is determined through the use of competitive binding assays. In this embodiment, the competitor is a binding moiety known to bind to the target protein, such as an antibody, peptide, binding partner, ligand, etc. Under certain circumstances, there may be competitive binding as between the candidate agent and the binding moiety, with the binding moiety displacing the candidate agent.

Competitive screening assays may be done by combining the target protein and a drug candidate in a first sample. A second sample comprises a candidate agent, the target protein and a compound that is known to modulate the target protein. This may be performed in either the presence or absence of microtubules. The binding of the candidate agent is determined for both samples, and a change, or difference in binding between the two samples indicates the presence of an agent capable of binding to the target protein and potentially modulating its activity. That is, if the binding of the candidate agent is different in the second sample relative to the first sample, the candidate agent is capable of binding to the target protein.

In one embodiment, the candidate agent is labeled. Either the candidate agent, or the competitor, or both, is added first to the target protein for a time sufficient to allow binding. Incubations may be performed at any temperature which facilitates optimal activity, typically between 4 and 40° C. Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate agent. Displacement of the competitor is an indication the candidate agent is binding to the target protein and thus is capable of binding to, and potentially modulating, the activity of the target protein. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to the target protein with a higher affinity. Thus, if the candidate agent is labeled, the presence of the label on the support, coupled with a lack of competitor binding, may indicate the candidate agent is capable of binding to the target protein.

C. Candidate Agents

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof Particularly preferred are peptides.

Candidate agents are obtained from a wide variety of sources including libraries of synthetic or natural compounds. In a preferred embodiment, the candidate agents are organic chemical moieties, a wide variety of which are available in the literature. Combinatorial libraries can be produced for many types of compounds that can be synthesized in a step-by-step fashion. Such compounds include polypeptides, proteins, nucleic acids, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of compounds can be constructed by the encoded synthetic libraries (ESL) method described in Affymax, WO 95/12608, Affymax WO 93/06121, Columbia University, WO 94/08051, Pharmacopeia, WO 95/35503 and Scripps, WO 95/30642 (each of which is incorporated herein by reference in its entirety for all purposes). Peptide libraries can also be generated by phage display methods. See, e.g., Devlin, WO 91/18980. Compounds to be screened can also be obtained from governmental or private sources, including, e.g., the National Cancer Institute's (NCI) Natural Product Repository, Bethesda, Md., the NCI Open Synthetic Compound Collection, Bethesda, Md., NCI's Developmental Therapeutics Program, or the like. Compounds to be screened can also be obtained from governmental or private sources, including, e.g., the National Cancer Institute's (NCI) Natural Product Repository, Bethesda, Md., the NCI Open Synthetic Compound Collection, Bethesda, Md., NCI's Developmental Therapeutics Program, or the like.

D. Other Assay Components

The assays provided utilize target protein as defined herein. In one embodiment, portions of target protein are utilized; in a preferred embodiment, portions having target protein activity as described herein are used. In addition, the assays described herein may utilize either isolated target proteins or cells or animal models comprising the target proteins.

A variety of other reagents may be included in the screening assays. These include reagents like salts, neutral proteins, e.g. albumin, detergents, etc which may be used to facilitate optimal protein—protein binding and/or reduce non-specific or background interactions. Also, reagents that otherwise improve the efficiency of the assay, such as protease inhibitors, nuclease inhibitors, anti-microbial agents, etc., may be used. The mixture of components may be added in any order that provides for the requisite binding.

VII. Applications

The methods of the invention are used to identify compounds useful in the treatment of cellular proliferation diseases. Disease states which can be treated by the methods and compositions provided herein include, but are not limited to, cancer (further discussed below), autoimmune disease, arthritis, graft rejection, inflammatory bowel disease, proliferation induced after medical procedures, including, but not limited to, surgery, angioplasty, and the like. It is appreciated that in some cases the cells may not be in a hyper or hypo proliferation state (abnormal state) and still require treatment. For example, during wound healing, the cells may be proliferating "normally", but proliferation enhancement may be desired. Similarly, as discussed above, in the agriculture arena, cells may be in a "normal" state, but proliferation modulation may be desired to enhance a crop by directly enhancing growth of a crop, or by inhibiting the growth of a plant or organism which adversely affects the crop. Thus, in one embodiment, the invention herein includes application to cells or individuals afflicted or impending affliction with any one of these disorders or states.

The compositions and methods provided herein are particularly deemed useful for the treatment of cancer including solid tumors such as skin, breast, brain, cervical carcinomas, testicular carcinomas, etc. More particularly, cancers that may be treated by the compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesotheliorna; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinorna, mucinous cystadenocarcinoma, unclassified carcinoma], granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above identified conditions.

Accordingly, the compositions of the invention are administered to cells. By "administered" herein is meant administration of a therapeutically effective dose of the candidate agents of the invention to a cell either in cell culture or in a patient. By "therapeutically effective dose"

herein is meant a dose that produces the effects for which it is administered. The exact dose will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art. By "cells" herein is meant almost any cell in which mitosis or meiosis can be altered.

A "patient" for the purposes of the present invention includes both humans and other animals, particularly mammals, and other organisms. Thus the methods are applicable to both human therapy and veterinary applications. In the preferred embodiment the patient is a mammal, and in the most preferred embodiment the patient is human.

Candidate agents having the desired pharmacological activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1–100 wt. %. The agents maybe administered alone or in combination with other treatments, i.e., radiation, or other chemotherapeutic agents.

In a preferred embodiment, the pharmaceutical compositions are in a water soluble form, such as pharmaceutically acceptable salts, which is meant to include both acid and base addition salts.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

The administration of the candidate agents of the present invention can be done in a variety of ways as discussed above, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the candidate agents may be directly applied as a solution or spray.

One of skill in the art will readily appreciate that the methods described herein also can be used for diagnostic applications. A diagnostic as used herein is a compound or method that assists in the identification and characterization of a health or disease state in humans or other animals.

The present invention also provides for kits for screening for modulators of the target protein. Such kits can be prepared from readily available materials and reagents. For example, such kits can comprise any one or more of the following materials: biologically active target protein, reaction tubes, and instructions for testing activity of the target protein. Preferably, the kit contains biologically active target protein. A wide variety of kits and components can be prepared according to the present invention, depending upon the intended user of the kit and the particular needs of the user. For example, the kit can be tailored for ATPase assays, microtubule gliding assays, or microtubule binding assays.

The kinesins of the present invention and in particular their motor domains can be used for separation of a specific ligand from a heterologous mixtures in aqueous solution as described by Stewart (U.S. Pat. No. 5,830,659. In the system discussed by Stewart, a kinesin motor domain is linked to a ligand binding moiety, such as streptavidin. The chimeric kinesin motor domains are placed into a loading chamber containing the heterogeneous mixtures which is coupled to a receiving chamber by a channel bearing immobilized, aligned microtubules. Addition of ATP to the loading chamber results in translocation of the kinesin motor domains, now attached non-covalently to the desired ligand via their ligand binding moiety, from the loading chamber to the receiving chamber. Hence, the ATP-driven motility activity of the kinesin motor domain results in separation of the desired ligand from the heterogeneous mixture. Stewart further teaches that all kinesin motor domains are suitable for use in the separation system.

The kinesins of the invention and in particular their motor domains can also be used in the field of nanotechnology. Molecular motors such as kinesin have widespread application in the construction of nanoscale machines. Biomolecular motors have real-world application in the emerging nanotechnological arts. For example, a 1999 NASA study identifies multiple applications for nanoscale motors—and kinesin in particular—in the aerospace field. Kinesin motor domains can be used in the construction of rotors and other mechanical components (for review see Limberis and Stewart, Nanotechnology 11:47–51(2000)) as well as light-operated molecular shuttles useful for nanoscale switches and pumps.

Nucleic acids encoding the kinesins of the invention are also useful for inclusion on a GeneChip™ array or the like for use in expression monitoring (see U.S. Pat. No. 6,040,138, EP 853, 679 and WO97/27317). Such arrays typically contain oligonucleotide or cDNA probes to allow detection of large numbers of mRNAs within a mixture. Many of the nucleic acids included in such arrays are from genes or ESTs that have not been well characterized. Such arrays are often used to compare expression profiles between different tissues or between different conditions of the same tissue (healthy vs. diseased or drug-treated vs. control) to identify differentially expressed transcripts. The differentially expressed transcripts are then useful e.g., for diagnosis of disease states, or to characterize responses of drugs. The nucleic acids of the invention can be included on Gene-Chip™ arrays or the like together with probes containing a variety of other genes. The present nucleic acids are particularly useful for inclusion in GeneChip™ arrays for analyzing the cell cycle or proliferation state of cells. Nucleic acids encoding hsKip3a can be combined with nucleic acids encoding other kinesin molecules and/or nucleic acids from other genes having roles in DNA replication, cell division or other cell cycle function. Such arrays are useful for analyzing and diagnosing cells in a proliferating state, and diseases such as cancer characterized by presence of the same. Such arrays are also useful for analyzing candidate drugs for roles in modulation of the cell cycle and proliferation. The efficacy of such drugs can be assayed by determining the effect of the drug on the expression profile of genes affecting proliferation and the cell cycle.

VIII. Examples

This assay is based on detection of ADP production from a target protein's microtubule stimulated ATPase. ATP production is monitored by a coupled enzyme system consisting of pyruvate kinase and lactate dehydrogenase. Under the assay conditions described below, pyruvate kinase catalyzes the conversion of ADP and phosphoenol pyruvate to pyruvate and ATP. Lactate dehydrogenase then catalyzes the oxidation-reduction reaction of pyruvate and NADH to lactate and NAD+. Thus, for each molecule of ADP produced, one molecule of NADH is consumed. The amount of NADH in the assay solution is monitored by measuring light absorbance at a wavelength of 340 nm.

The final 25 μl assay solution consists of the following: 5 μg/ml target protein, 30 μg/ml microtubules, 5 μM Taxol, 0.8 mM NADH, 1.5 mM phosphoenol pyruvate, 3.5 U/ml pyruvate kinase, 5 U/ml lactate dehydrogenase, 25 mM Pipes/KOH pH 6.8, 2 mM MgCl$_2$, 1 mM EGTA, 1 mM MDTT, 0.1 mg/ml BSA, 0.001% antifoam 289, and 1 mMATP.

Potential candidate agents are dissolved in DMSO at a concentration of about 1 mg/ml and 0.5 μl of each chemical solution is dispensed into a single well of a clear 384 well plate. Each of the 384 wells are then filled with 20 μl of a solution consisting of all of the assay components described above except for ATP. The plate is agitated at a high frequency. To start the assay, 5 μl of a solution containing ATP is added to each well. The plate is agitated and the absorbance is read at 340 nm over various time intervals. The assay is run at room temperature.

The assay components and the performance of the assay are optimized together to match the overall read time with the rate of the target protein's ADP production. The read time should be long enough for the rate of NADH consumption to reach steady state beyond an initial lag time of several seconds.

EXAMPLES

ATPase Assay Protocol 2 ug/ml Kip3A 353 protein was assayed for its microtubule-stimulated ATP-ase activity in the reaction buffer composed of 40 uM MES/KOH pH6.8, 2 mM MgCl2, 1 mM DTT, 1 mM EGTA, 100 uM ATP, 10 uM paclitaxel, 0.1 mg/mlBSA, 0.5 mM NADH, 1.5 mM phosphoenolpyruvate, lactate dehydrogenase/pyruvate kinase mix (Sigma, diluted 1:200 v/v final) and varied amounts of microtubules (from 50 ug/ml to 24 ng/ml). The reaction progress was followed up over time by monitoring absorbance of the reaction mix at 340 nm using microtiter plate reader (SpectraMAX340, Molecular Devices Inc.) The rate of the absorbance change was converted to uM NADH oxidized per second by referencing it to a set of standard NADH solutions of known concentrations. In this coupled ATPase assay conversion of one NADH to NAD+ reports appearance of one ADP molecule, and as such reports a single turnover of Kip3A ATPase.

FIG. 6 presents the summary of the results from the above assay. Each data point is an average of two separate measurements. The data points were fitted to the Michaelis-Menten kinetic equation using nonlinear fitting program Grafit (Erithacus Software Inc) Obtained fit indicated Km for microtubule stimulation of 4.6 ug/ml and Vmax 0.85 uM ADP/s which corresponds to a kcat value of $15s^-$

Expression Profiling of Kip3a

A real time quantitative PCR assay (TaqMan™, Applied Biosystems) was developed to specifically measure Kip3 a mRNA levels in human tissues and cell lines in order to assess the biological function of Kip3 a. Previously, we have shown that kinesins involved in mitosis such as human KSP are up regulated in tumor versus normal tissue and that their expression is correlated with the proliferation index of cells.

Conversely, the expression level of kinesins not involved in mitosis is not correlated with proliferation or mitotic index.

The expression profile of Kip3a in various tissues is shown in FIG. 7. Abbreviations are as follows:
CA: cancer
NAT: Normal Adjacent Tissue
IMR90 65%: IMR90 cells harvested at 65% confluence
IMR90 Fed: IMR90n cells harvested after being confluent for 4 days
IMR90 starved: IMR90 cells harvested after being confluent and serum starved for 4 days
NT2 Undiff: NT2 cells undifferentiated in proliferating
NT2 diff: NT2 cells differentiated into post-mitotic neurons
Y axis: relative level of expression normalized to HeLa cells Kip3a expression was clearly up regulated in lung, colon and breast tumors (top graphs and bottom left graph, compare the orange bar to the adjacent blue bar), the fold induction between the normal and tumor matched-pairs is indicated in red. Kip3a expression is also correlated with the proliferation status of IMR90 and NT2 cells. Indeed, when IMR90 cells are kept confluent and/or serum starved, the number of proliferating cells decreases, as does the expression level of Kip3a (bottom right bar graph, blue bars). Similarly, expression of Kip3a is elevated in proliferating NT2 cells but dramatically decreases when these cells are fully differentiated in post mitotic neurons (bottom right bar graph, yellow bars). The expression profile of Kip3a indicates that it is involved in the cell division process.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety.

What is claimed is:

1. An isolated microtubule motor protein, wherein the protein (i) has greater than 90% amino acid sequence identity to SEQ ID NO:2 or SEQ ID NO:4 as measured using a sequence comparison algorithm, and (ii) has microtubule-stimulated ATPase activity, ATP-dependent microtubule motor activity and/or microtubule binding activity.

2. The isolated protein of claim 1, wherein the protein specifically binds to polyclonal antibodies to proteins having the amino acid sequence of SEQ ID NO:2 or SEQ ID NO:4.

3. The isolated protein of claim 1, wherein the protein has the amino acid sequence of SEQ ID NO:2.

4. The isolated protein of claim 1, wherein the protein has the amino acid sequence SEQ ID NO:4.

5. The isolated protein of claim 1, wherein the protein specifically binds to polyclonal antibodies generated against a motor domain of HsKip3a, said domain comprising amino acids 5–342 or 26–354 of SEQ ID NO:2.

6. The isolated protein of claim 1, wherein the protein comprises the amino acid sequence of a HsKip3a motor domain, said domain comprising amino acids 5–342 or 26–354 of SEQ ID NO:2.

7. The isolated protein of claim 1, wherein the protein has greater than 95% amino acid sequence identity to SEQ ID NO:2 or SEQ ID NO:4.

8. The isolated protein of claim 1, wherein the protein has greater than 98% amino acid sequence identity to SEQ ID NO:2 or SEQ ID NO:4.

9. T The isolated protein of claim 1, wherein the protein has microtubule-stimulated ATPase activity.

10. The isolated protein of claim 1, wherein the protein has ATP-dependent microtubule motor activity.

11. The isolated protein of claim 1, wherein the protein has microtubule binding activity.

* * * * *

SEQUENCE LISTING

<160> NUMBER OF SEQ ID NOS: 6

<210> SEQ ID NO 1
<211> LENGTH: 4108
<212> TYPE: DNA
<213> ORGANISM: Artificial Sequence
<220> FEATURE:
<223> OTHER INFORMATION: Nucleic acid sequence of human kinesin motor protein gene HsKip3a (Figure 1).

<223> OTHER INFORMATION: Description of Artificial Sequence: HsKip3a gene.

<400> SEQUENCE: 1

```
gcggccgcga attcggcacc aggggcgctc tctcccggtg tgggtactgc tgtctgtggt    60
gtggctgtgg gacccgtgag caagcagcga cgccagcggc ggagaaccga cgaaaggtgt   120
caccacagtg atggcagtgg aggacagcac gctgcaagta gtggtacggg tgcggccccc   180
caccectcgg gagctggaca gtcagcggcg gccagtggtt caggtggtgg acgagcgggt   240
gctggtgttt aaccctgagg agcccgatgg agggttccct ggcctgaaat ggggtggcac   300
ccatgatggc cccaagaaga agggcaaaga cctgacgttt gtctttgacc gggtctttgg   360
cgaggcggcc acccaacagg acgtgttcca gcacaccacg cacagcgtcc tggacagctt   420
cctccagggc tacaactgct cagtgtttgc ctacggggcc accggggctg ggaagacaca   480
caccatgctg ggaagggagg gggacccccg catcatgtac ctgaccaccg tggaactgta   540
caggcgcctg gaggcccgcc agcaggagaa gcacttcgag gtgctcatca gctaccagga   600
ggtgtataat gaacagatcc atgacctcct ggagcccaag gggccccttg ccatccgcga   660
ggacccccgac aagggggtgg tggtgcaagg actttctttc caccagccag cctcagccga   720
gcagctgctg gagatactga ccaggggaa ccgtaaccgc acgcagcacc ccactgatgc   780
caacgcgact tcctcccgct cccatgccat cttccagatc tttgtgaagc agcaggaccg   840
ggttccagga ctgacccagg ctgtccaggt ggccaagatg agcctgattg acctggctgg   900
ctcagagcgg gcatccagca cccatgcgaa ggggagcgg ctgcggagg gggccaacat    960
caaccgctct ctgctggcgc tcatcaacgt cctcaatgcc ttggccgatg caaagggccg  1020
caagacccat gtgccctacc gggacagcaa actgaccccg ctgctcaaag actccctcgg  1080
gggcaactgc cgcacagtga tgatcgctgc catcagcccc tccagcctga cctacgagga  1140
cacgtacaac accctcaaat atgccgaccg ggccaaggag atcaggctct cgctgaagag  1200
caatgtgacc agcctggact gtcacatcag ccagtatgct accatctgcc aacagctcca  1260
ggctgaggta ccgctctga ggaagaagct ccaagtgtat gagggggag ccagccccc   1320
accacaggac ctcccaggat ctcccaagtc gggaccacca ccagaacacc ttcccagctc  1380
cccccttgcca ccccaccctc ccagccagcc ctgcacccca gagctccctg cagggcctag  1440
agcccttcaa gaggagagtc tggggatgga ggcccaggtg gagagggcca tggaagggaa  1500
ctcttcagac caggagcagt ccccagagga tgaggatgaa ggcccagctg aggaggttcc  1560
aacccagatg ccagagcaga accccacaca tgcactgcca gagtcccctc gcctgaccct  1620
gcagcccaag ccagtcgtgg gccacttctc agcacgggaa ctggatgggg accgttctaa  1680
gcagttggcc ctaaaggtgc tgtgcgttgc ccagcggcag tactccctgc tccaagcagc  1740
caacctcctg acgcccgaca tgatcacaga gtttgagacc ctacagcagc tggtgcaaga  1800
ggaaaaaatt gagcctgggg cagaggcctt gaggacttca ggcctggcca gggggggcacc  1860
tctggctcag gagctgtgtt cagagtcaat ccctgtgccg tctcctctct gcccagagcc  1920
tccaggatac actggccctg tgacccggac tatggcgagg cgactgagtg ccccctgca   1980
cacccctggga atcccgcctg gacccaactg caccccagcc cagggtccc gatgcccat   2040
ggagaagaag aggaggagac caagcgcctt ggaggcagac agtcccatgg cctcaaagcg  2100
gggcaccaag cgccagcgcc agtccttcct gccctgccta aggagagggt ctctgcctga  2160
cacccaacct tcagggggc ccagcacccc caaaggagaa agggcctcct cccctgcca   2220
ttccctcgc gtttgcccag ccacagtcat caaaagccgg gtgccctgg gcccttccgc  2280
```

-continued

```
catgcagaac tgctccaccc cgctggctct gcccactcga gacctcaatg ccacctttga    2340
tctctctgag gagcctccct caaagcccag tttccatgaa tgcattggct gggacaaaat    2400 acccaggag ctgagcaggc tggaccagcc cttcatcccc agggcacctg tgcccctgtt     2460
caccatgaag ggccccaagc caacatcttc cctccctggg acctctgcct gcaagaagaa    2520
gcgcgttgcg agttcctcag tctcccatgg ccgcagccgc atcgcccgcc tccccagcag    2580
cactttgaag aggccagctg ggccccttgt actcccagag ctgcccttga gtccctgtg     2640 ccctagcaac cggaggaatg gaaaggacct catcagggtg gggagagcgc tctcagcagg    2700
gaacggcgtc accaaggtgt cctgaccgcc agaatgtcct gaccaccaag gtgtcctaac    2760
ctaccggccc ctctgctgga taccctctt ggacctgtag ccacctgcac caggagctgg     2820
acctgccttc cttacctggg agcaattagt gccaacacac ctttgctgta ttaacatccc    2880
tccccagaca tccatcctgc tactcaccct ctgttaatct cctgttacac tcagcttctt    2940
ggcatgtaca tattcatttg tgagtgttaa tgtgctgctg ttttttgttt tttggtggtt    3000
tttgtttttt gtttttttg ttttgagatg gagtcttact ctgtcgccca ggctggagtg     3060
cagtggtacg atcttggctc actgcaacct ccgcctcctg ggttcaagta attctcctgc    3120
ctcagctttc caagtagctg ggattacagg cacccatcac cacacccagc taattttcgt    3180 cttttaata gagaggggt ttttccatgt tggccaggct ggtcttgaac tcctgacctc       3240
aggtgatccg cctgcctcag cttcccaaag tgctgagatt acaggcatga gctaccacgc    3300
ctggcccgtg ttgctgtttt aaaggtgctg ccatgttccc ccatcttttt ttttttgag     3360 atggagtctc gctctgtcgc ccaggctgga gtgcagtggt ggcgatcttg gctcactgca    3420
agctccgcct cccaggttca caccattctc ctgcctcagc ctcccaagta gctgggacta    3480
caggcgccca ccaccacgcc cggctaattt tttgtatttt tagtagagat ggggtttcac    3540
cgtgttagcc aggctggtct cgatctgacc tcatgatcca cccgcctcgg cctcccaaag    3600
tgctgggatt acaggcgtga gccactcgcg ccggcctccc ctctcattta tgatgccctc    3660
tgtgcaggca gacggctctt gggctctttt ccccacctgt ctctaacaca ggccccacgg    3720
tgatggccac aggcagtaga ggaggaatga ggatgggttg gggagcgggg agtcgcggct    3780
tggctcttcc tggtttctga gagggacatc ttcatcccta ctccccttgg tccccaacca    3840
cagtcctggt gaagatgtgg atgataatgg tgccttgatt tccaaatgaa gacagcttta    3900
ttgcttaact ctattgtaca taggatacac gttcagtgta aaataaagtg taaaggggaa    3960
ttcaggctta atgctgcacc tagatataaa tgctaatgat acttgggttt atagccttct    4020
gatcctttat ttctgcatat atatatagat atatacatat attttggta taacaataaa     4080 ccgtctccat ccttgggaaa aaaaaaaa                                       4108
```

<210> SEQ ID NO 2
<211> LENGTH: 864
<212> TYPE: PRT
<213> ORGANISM: Artificial Sequence
<220> FEATURE:
<223> OTHER INFORMATION: Amino acid sequence encoded by human kinesin motor protein gene HsKip3a (Figure 1).
<223> OTHER INFORMATION: Description of Artificial Sequence:Amino acid sequence of HsKip3a.

<400> SEQUENCE: 2

```
Met Ala Val Glu Asp Ser Thr Leu Gln Val Val Arg Val Arg Pro
 1               5                  10                  15
```

-continued

```
Pro Thr Pro Arg Glu Leu Asp Ser Gln Arg Arg Pro Val Val Gln Val
         20                  25                  30

Val Asp Glu Arg Val Leu Val Phe Asn Pro Glu Pro Asp Gly Gly
             35                  40                  45

Phe Pro Gly Leu Lys Trp Gly Gly Thr His Asp Gly Pro Lys Lys Lys
     50                  55                  60

Gly Lys Asp Leu Thr Phe Val Phe Asp Arg Val Phe Gly Glu Ala Ala
 65                  70                  75                  80

Thr Gln Gln Asp Val Phe Gln His Thr Thr His Ser Val Leu Asp Ser
                 85                  90                  95

Phe Leu Gln Gly Tyr Asn Cys Ser Val Phe Ala Tyr Gly Ala Thr Gly
            100                 105                 110

Ala Gly Lys Thr His Thr Met Leu Gly Arg Glu Gly Asp Pro Gly Ile
        115                 120                 125

Met Tyr Leu Thr Thr Val Glu Leu Tyr Arg Arg Leu Glu Ala Arg Gln
    130                 135                 140

Gln Glu Lys His Phe Glu Val Leu Ile Ser Tyr Gln Glu Val Tyr Asn
145                 150                 155                 160

Glu Gln Ile His Asp Leu Leu Glu Pro Lys Gly Pro Leu Ala Ile Arg
                165                 170                 175

Glu Asp Pro Asp Lys Gly Val Val Gln Gly Leu Ser Phe His Gln
            180                 185                 190

Pro Ala Ser Ala Glu Gln Leu Leu Glu Ile Leu Thr Arg Gly Asn Arg
        195                 200                 205

Asn Arg Thr Gln His Pro Thr Asp Ala Asn Ala Thr Ser Ser Arg Ser
    210                 215                 220

His Ala Ile Phe Gln Ile Phe Val Lys Gln Asp Arg Val Pro Gly
225                 230                 235                 240

Leu Thr Gln Ala Val Gln Val Ala Lys Met Ser Leu Ile Asp Leu Ala
                245                 250                 255

Gly Ser Glu Arg Ala Ser Ser Thr His Ala Lys Gly Glu Arg Leu Arg
            260                 265                 270

Glu Gly Ala Asn Ile Asn Arg Ser Leu Leu Ala Leu Ile Asn Val Leu
        275                 280                 285

Asn Ala Leu Ala Asp Ala Lys Gly Arg Lys Thr His Val Pro Tyr Arg
    290                 295                 300

Asp Ser Lys Leu Thr Arg Leu Leu Lys Asp Ser Leu Gly Gly Asn Cys
305                 310                 315                 320

Arg Thr Val Met Ile Ala Ala Ile Ser Pro Ser Ser Leu Thr Tyr Glu
                325                 330                 335

Asp Thr Tyr Asn Thr Leu Lys Tyr Ala Asp Arg Ala Lys Glu Ile Arg
            340                 345                 350

Leu Ser Leu Lys Ser Asn Val Thr Ser Leu Asp Cys His Ile Ser Gln
        355                 360                 365

Tyr Ala Thr Ile Cys Gln Gln Leu Gln Ala Glu Val Ala Ala Leu Arg
    370                 375                 380

Lys Lys Leu Gln Val Tyr Glu Gly Gly Gln Pro Pro Gln Asp
385                 390                 395                 400

Leu Pro Gly Ser Pro Lys Ser Gly Pro Pro Glu His Leu Pro Ser
                405                 410                 415

Ser Pro Leu Pro Pro His Pro Pro Ser Gln Pro Cys Thr Pro Glu Leu
            420                 425                 430

Pro Ala Gly Pro Arg Ala Leu Gln Glu Glu Ser Leu Gly Met Glu Ala
```

```
            435                 440                 445
Gln Val Glu Arg Ala Met Glu Gly Asn Ser Ser Asp Gln Glu Gln Ser
    450                 455                 460
Pro Glu Asp Glu Asp Gly Pro Ala Glu Glu Val Pro Thr Gln Met
465                 470                 475                 480
Pro Glu Gln Asn Pro Thr His Ala Leu Pro Glu Ser Pro Arg Leu Thr
                485                 490                 495
Leu Gln Pro Lys Pro Val Val Gly His Phe Ser Ala Arg Glu Leu Asp
            500                 505                 510
Gly Asp Arg Ser Lys Gln Leu Ala Leu Lys Val Leu Cys Val Ala Gln
        515                 520                 525
Arg Gln Tyr Ser Leu Leu Gln Ala Ala Asn Leu Leu Thr Pro Asp Met
    530                 535                 540
Ile Thr Glu Phe Glu Thr Leu Gln Gln Leu Val Gln Glu Glu Lys Ile
545                 550                 555                 560
Glu Pro Gly Ala Glu Ala Leu Arg Thr Ser Gly Leu Ala Arg Gly Ala
                565                 570                 575
Pro Leu Ala Gln Glu Leu Cys Ser Glu Ser Ile Pro Val Pro Ser Pro
            580                 585                 590
Leu Cys Pro Glu Pro Pro Gly Tyr Thr Gly Pro Val Thr Arg Thr Met
        595                 600                 605
Ala Arg Arg Leu Ser Gly Pro Leu His Thr Leu Gly Ile Pro Pro Gly
    610                 615                 620
Pro Asn Cys Thr Pro Ala Gln Gly Ser Arg Trp Pro Met Glu Lys Lys
625                 630                 635                 640
Arg Arg Arg Pro Ser Ala Leu Glu Ala Asp Ser Pro Met Ala Ser Lys
                645                 650                 655
Arg Gly Thr Lys Arg Gln Arg Gln Ser Phe Leu Pro Cys Leu Arg Arg
            660                 665                 670
Gly Ser Leu Pro Asp Thr Gln Pro Ser Gln Gly Pro Ser Thr Pro Lys
        675                 680                 685
Gly Glu Arg Ala Ser Ser Pro Cys His Ser Pro Arg Val Cys Pro Ala
    690                 695                 700
Thr Val Ile Lys Ser Arg Val Pro Leu Gly Pro Ser Ala Met Gln Asn
705                 710                 715                 720
Cys Ser Thr Pro Leu Ala Leu Pro Thr Arg Asp Leu Asn Ala Thr Phe
                725                 730                 735
Asp Leu Ser Glu Glu Pro Ser Lys Pro Ser Phe His Glu Cys Ile
            740                 745                 750
Gly Trp Asp Lys Ile Pro Gln Glu Leu Ser Arg Leu Asp Gln Pro Phe
        755                 760                 765
Ile Pro Arg Ala Pro Val Pro Leu Phe Thr Met Lys Gly Pro Lys Pro
    770                 775                 780
Thr Ser Ser Leu Pro Gly Thr Ser Ala Cys Lys Lys Arg Val Ala
785                 790                 795                 800
Ser Ser Ser Val Ser His Gly Arg Ser Arg Ile Ala Arg Leu Pro Ser
                805                 810                 815
Ser Thr Leu Lys Arg Pro Ala Gly Pro Leu Val Leu Pro Glu Leu Pro
            820                 825                 830
Leu Ser Pro Leu Cys Pro Ser Asn Arg Arg Asn Gly Lys Asp Leu Ile
        835                 840                 845
Arg Val Gly Arg Ala Leu Ser Ala Gly Asn Gly Val Thr Lys Val Ser
    850                 855                 860
```

<210> SEQ ID NO 3
<211> LENGTH: 1014
<212> TYPE: DNA
<213> ORGANISM: Artificial Sequence
<220> FEATURE:
<223> OTHER INFORMATION: Description of Artificial Sequence: HsKip3a fragment
<223> OTHER INFORMATION: Nucleotide sequence encoding motor domain fragment of HsKip3a (Figure 2).

<400> SEQUENCE: 3

```
gacagcacgc tgcaagtagt ggtacgggtg cggcccccca cccctcggga gctggacagt    60
cagcggcggc cagtggttca ggtggtggac gagcgggtgc tggtgtttaa ccctgaggag   120
cccgatggag ggttccctgg cctgaaatgg ggtggcaccc atgatggccc caagaagaag   180
ggcaaagacc tgacgtttgt ctttgaccgg gtctttggcg aggcggccac caacaggac    240
gtgttccagc acaccacgca cagcgtcctg gacagcttcc tccagggcta caactgctca   300
gtgtttgcct acggggccac cggggctggg aagacacaca ccatgctggg aagggagggg   360
gaccccggca tcatgtacct gaccaccgtg gaactgtaca ggcgcctgga ggcccgccag   420
caggagaagc acttcgaggt gctcatcagc taccaggagg tgtataatga acagatccat   480
gacctcctgg agcccaaggg gccccttgcc atccgcgagg accccgacaa ggggtggtg    540
gtgcaaggac tttctttcca ccagccagcc tcagccgagc agctgctgga gatactgacc   600
agggggaacc gtaaccgcac gcagcacccc actgatgcca acgcgacttc ctcccgctcc   660
catgccatct tccagatctt tgtgaagcag caggaccggg ttccaggact gacccaggct   720
gtccaggtgg ccaagatgag cctgattgac ctggctggct cagagcgggc atccagcacc   780
catgcgaagg gggagcggct gcgggagggg gccaacatca accgctctct gctggcgctc   840
atcaacgtcc tcaatgcctt ggccgatgca aagggccgca agacccatgt gccctaccgg   900
gacagcaaac tgacccgcct gctcaaagac tccctcgggg caactgccg cacagtgatg   960
atcgctgcca tcagcccctc cagcctgacc tacgaggaca cgtacaacac cctc        1014
```

<210> SEQ ID NO 4
<211> LENGTH: 338
<212> TYPE: PRT
<213> ORGANISM: Artificial Sequence
<220> FEATURE:
<223> OTHER INFORMATION: Description of Artificial Sequence: HsKip3a fragment.
<223> OTHER INFORMATION: Amino acid sequence of the motor domain fragment of HsKip3a (Figure 3).

<400> SEQUENCE: 4

```
Asp Ser Thr Leu Gln Val Val Arg Val Arg Pro Pro Thr Pro Arg
  1               5                  10                  15

Glu Leu Asp Ser Gln Arg Arg Pro Val Val Gln Val Val Asp Glu Arg
                 20                  25                  30

Val Leu Val Phe Asn Pro Glu Glu Pro Asp Gly Gly Phe Pro Gly Leu
             35                  40                  45

Lys Trp Gly Gly Thr His Asp Gly Pro Lys Lys Gly Lys Asp Leu
         50                  55                  60

Thr Phe Val Phe Asp Arg Val Phe Gly Glu Ala Ala Thr Gln Gln Asp
 65                  70                  75                  80

Val Phe Gln His Thr Thr His Ser Val Leu Asp Ser Phe Leu Gln Gly
                 85                  90                  95
```

```
Tyr Asn Cys Ser Val Phe Ala Tyr Gly Ala Thr Gly Ala Gly Lys Thr
            100                 105                 110

His Thr Met Leu Gly Arg Glu Gly Asp Pro Gly Ile Met Tyr Leu Thr
            115                 120                 125

Thr Val Glu Leu Tyr Arg Arg Leu Glu Ala Arg Gln Gln Glu Lys His
            130                 135                 140

Phe Glu Val Leu Ile Ser Tyr Gln Glu Val Tyr Asn Glu Gln Ile His
145                 150                 155                 160

Asp Leu Leu Glu Pro Lys Gly Pro Leu Ala Ile Arg Glu Asp Pro Asp
                165                 170                 175

Lys Gly Val Val Gln Gly Leu Ser Phe His Gln Pro Ala Ser Ala
                180                 185                 190

Glu Gln Leu Leu Glu Ile Leu Thr Arg Gly Asn Arg Asn Arg Thr Gln
            195                 200                 205

His Pro Thr Asp Ala Asn Ala Thr Ser Ser Arg Ser His Ala Ile Phe
            210                 215                 220

Gln Ile Phe Val Lys Gln Gln Asp Arg Val Pro Gly Leu Thr Gln Ala
225                 230                 235                 240

Val Gln Val Ala Lys Met Ser Leu Ile Asp Leu Ala Gly Ser Glu Arg
                245                 250                 255

Ala Ser Ser Thr His Ala Lys Gly Glu Arg Leu Arg Glu Gly Ala Asn
            260                 265                 270

Ile Asn Arg Ser Leu Leu Ala Leu Ile Asn Val Leu Asn Ala Leu Ala
            275                 280                 285

Asp Ala Lys Gly Arg Lys Thr His Val Pro Tyr Arg Asp Ser Lys Leu
            290                 295                 300

Thr Arg Leu Leu Lys Asp Ser Leu Gly Gly Asn Cys Arg Thr Val Met
305                 310                 315                 320

Ile Ala Ala Ile Ser Pro Ser Ser Leu Thr Tyr Glu Asp Thr Tyr Asn
                325                 330                 335

Thr Leu

<210> SEQ ID NO 5
<211> LENGTH: 383
<212> TYPE: PRT
<213> ORGANISM: Artificial Sequence
<220> FEATURE:
<223> OTHER INFORMATION: Description of Artificial Sequence: HsKip3a
      fragment
<223> OTHER INFORMATION: Amino acid sequence of HsKip3a fragment used in
      the ATPase assay (Figure 4).

<400> SEQUENCE: 5

Met Ala Val Glu Asp Ser Thr Leu Gln Val Val Arg Val Arg Pro
1               5                   10                  15

Pro Thr Pro Arg Glu Leu Asp Ser Gln Arg Arg Pro Val Gln Val
                20                  25                  30

Val Asp Glu Arg Val Leu Val Phe Asn Pro Glu Glu Pro Asp Gly Gly
            35                  40                  45

Phe Pro Gly Leu Lys Trp Gly Gly Thr His Asp Gly Pro Lys Lys Lys
    50                  55                  60

Gly Lys Asp Leu Thr Phe Val Phe Asp Arg Val Phe Gly Glu Ala Ala
65                  70                  75                  80

Thr Gln Gln Asp Val Phe Gln His Thr Thr His Ser Val Leu Asp Ser
                85                  90                  95

Phe Leu Gln Gly Tyr Asn Cys Ser Val Phe Ala Tyr Gly Ala Thr Gly
```

```
                    100                 105                 110
Ala Gly Lys Thr His Thr Met Leu Gly Arg Glu Gly Asp Pro Gly Ile
        115                 120                 125

Met Tyr Leu Thr Thr Val Glu Leu Tyr Arg Arg Leu Glu Ala Arg Gln
    130                 135                 140

Gln Glu Lys His Phe Glu Val Leu Ile Ser Tyr Gln Glu Val Tyr Asn
145                 150                 155                 160

Glu Gln Ile His Asp Leu Leu Glu Pro Lys Gly Pro Leu Ala Ile Arg
                165                 170                 175

Glu Asp Pro Asp Lys Gly Val Val Gln Gly Leu Ser Phe His Gln
            180                 185                 190

Pro Ala Ser Ala Glu Gln Leu Leu Glu Ile Leu Thr Arg Gly Asn Arg
        195                 200                 205

Asn Arg Thr Gln His Pro Thr Asp Ala Asn Ala Thr Ser Ser Arg Ser
    210                 215                 220

His Ala Ile Phe Gln Ile Phe Val Lys Gln Gln Asp Arg Val Pro Gly
225                 230                 235                 240

Leu Thr Gln Ala Val Gln Val Ala Lys Met Ser Leu Ile Asp Leu Ala
                245                 250                 255

Gly Ser Glu Arg Ala Ser Ser Thr His Ala Lys Gly Glu Arg Leu Arg
            260                 265                 270

Glu Gly Ala Asn Ile Asn Arg Ser Leu Leu Ala Leu Ile Asn Val Leu
        275                 280                 285

Asn Ala Leu Ala Asp Ala Lys Gly Arg Lys Thr His Val Pro Tyr Arg
    290                 295                 300

Asp Ser Lys Leu Thr Arg Leu Leu Lys Asp Ser Leu Gly Gly Asn Cys
305                 310                 315                 320

Arg Thr Val Met Ile Ala Ala Ile Ser Pro Ser Ser Leu Thr Tyr Glu
                325                 330                 335

Asp Thr Tyr Asn Thr Leu Lys Tyr Ala Asp Arg Ala Lys Glu Ile Arg
            340                 345                 350

Leu Lys Gly Asn Ser Lys Leu Glu Gly Lys Pro Ile Pro Asn Pro Leu
        355                 360                 365

Leu Gly Leu Asp Ser Thr Arg Thr Gly His His His His His
    370                 375                 380
```

<210> SEQ ID NO 6
<211> LENGTH: 1152
<212> TYPE: DNA
<213> ORGANISM: Artificial Sequence
<220> FEATURE:
<223> OTHER INFORMATION: Description of Artificial Sequence: HsKip3a
      fragment
<223> OTHER INFORMATION: Nucleotide sequence of HsKip3a fragment used in
      ATPase assay (Figure 5).

<400> SEQUENCE: 6
atggcagtgg aggacagcac gctgcaagta gtggtacggg tgcggccccc cacccctcgg      60
gagctggaca gtcagcggcg gccagtggtt caggtggtgg acgagcgggt gctggtgttt     120
aaccctgagg agcccgatgg agggttccct ggcctgaaat gggtggcac ccatgatggc      180 cccaagaaga agggcaaaga cctgacgttt gtctttgacc gggtctttgg cgaggcggcc     240
acccaacagg acgtgttcca gcacaccacg cacagcgtcc tggacagctt cctccagggc     300
tacaactgct cagtgtttgc ctacggggcc accgggctg gaagacaca ccatgctg         360 ggaagggagg gggaccccgg catcatgtac ctgaccaccg tggaactgta caggcgcctg     420

-continued

```
gaggcccgcc agcaggagaa gcacttcgag gtgctcatca gctaccagga ggtgtataat    480
gaacagatcc atgacctcct ggagcccaag gggcccttg ccatccgcga ggaccccgac     540
aaggggtgg tggtgcaagg actttctttc caccagccag cctcagccga gcagctgctg     600
gagatactga ccaggggaa ccgtaaccgc acgcagcacc ccactgatgc caacgcgact     660
tcctcccgct cccatgccat cttccagatc tttgtgaagc agcaggaccg ggttccagga    720
ctgacccagg ctgtccaggt ggccaagatg agcctgattg acctggctgg ctcagagcgg    780
gcatccagca cccatgcgaa gggggagcgg ctgcgggagg gggccaacat caaccgctct    840
ctgctggcgc tcatcaacgt cctcaatgcc ttggccgatg caaagggccg caagacccat    900
gtgccctacc gggacagcaa actgacccgc ctgctcaaag actccctcgg gggcaactgc    960
cgcacagtga tgatcgctgc catcagcccc tccagcctga cctacgagga cacgtacaac   1020
accctcaaat atgccgaccg ggccaaggag atcaggctca agggcaattc gaagcttgaa   1080
ggtaagccta tccctaaccc tctcctcggt ctcgattcta cgcgtaccgg tcatcatcac   1140
catcaccatt ga                                                       1152
```